US009388143B2

(12) United States Patent
Baulier et al.

(10) Patent No.: US 9,388,143 B2
(45) Date of Patent: Jul. 12, 2016

(54) POLYMORPH OF N-(3-{[(2Z)-3-[(2-CHLORO-5-METHOXYPHENYL)AMINO]QUINOXALIN-2(1H)-YLIDENE]SULFAMOYL}PHENYL)-2-METHYLALANINAMIDE

(71) Applicant: Sanofi, Paris (FR)

(72) Inventors: Virginie Baulier, Volx (FR); Matthieu Fugier, Sourribes (FR); Stephane Kozlovic, Sisteron (FR); Marc-Antoine Perrin, Jouy-en-Josas (FR); Bruno Baillon, Le Poet (FR); Myriam Comte, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/645,937

(22) Filed: Mar. 12, 2015

(65) Prior Publication Data

US 2015/0183752 A1    Jul. 2, 2015

Related U.S. Application Data

(63) Continuation of application No. PCT/EP2013/069068, filed on Sep. 13, 2013.

(60) Provisional application No. 61/700,618, filed on Sep. 13, 2012.

(30) Foreign Application Priority Data

Jun. 28, 2013 (FR) ...................... 13 56284

(51) Int. Cl.
*A61K 31/498* (2006.01)
*C07D 241/44* (2006.01)

(52) U.S. Cl.
CPC .................................. *C07D 241/44* (2013.01)

(58) Field of Classification Search
CPC ........................... A61K 31/498; C07D 241/44
USPC .......................................... 514/249; 544/356
See application file for complete search history.

(56) References Cited

FOREIGN PATENT DOCUMENTS

| WO | WO 2007/044729 | 4/2007 |
| WO | WO 2013/067141 | 5/2013 |
| WO | WO 2014/041142 | * 3/2014 |

OTHER PUBLICATIONS

Jordan, V. C. Nature Reviews: Drug Discovery, 2, 2003, 205.*
Hackam, et al. JAMA, 296(14), 2006, 1731-1732.*
International Search Report for WO2014/041144 dated Mar. 30, 2014.
Guillory, Generation of Polymorphs, Hydrates, Solvates, and Amorphous Solids, Polymorphism in Pharmaceutical Solids; Drugs and the Pharmaceutical Sciences; 95, p. 183-225, (1999).
Sridhar, et al., Protein Kinases as Therapeutic Targets, Pharmaceutical Research, vol. 17, No. 11, (2000), pp. 1345-1353.
Park, et al., A Novel Mechanism of TRAF Signaling Revealed by Structural and Functional Analyses of the TRADD-TRAF2 Interaction, Cell, vol. 101, pp. 777-787. (2000).
Campbell, et al., Mutation of the PIK3CA Gene in Ovarian and Breast Cancer, Cancer Research. vol. 64, pp. 7678-7681, (2004).
Levine, et al., Frequent Mutation of the PIK3CA Gene in Ovarian, Clin Cancer Res. (2005), vol. 11, No. 8, (2005), pp. 2875-2878.
Wang, et al., PIK3CA Mutations in Advanced Ovarian Carcinomas. Human Mutation. (2005), vol. 25, p 1-5.
Lee, et al,. Activation of PI3K/Akt Pathway by PTEN Reduction and PIK3CAS MRNA Amplification Contributes to Cisplatin Resistance in an Ovarian Cancer Cell Line, Gynecologic Oncology, vol. 97, (2008), pp. 26-34.
Li, et al., PIK3CA Mutations in Breast Cancer are Associated With Poor Outcome, Breast Cancer Research and Treatment, (2006). vol. 95, pp. 91-95.
Saal, et al., PIK3CA Mutations Correlate With Hormone Receptors, Node Metastasis, and ERBB2, and Are Mutually Exclusive With PTEN Loss in Human Breast Carcinoma, Cancer Research, (2005), vol. 65, No. 7, pp. 2554-2559.
Samuels, et al., High Frequency of Mutations of th PIK3CA Gene in Human Cancers, Science, (2004), vol. 304, p. 554.
Velho, et al., The Prevalence of PIK3CA Mutations in Gastric and Colon Cancer, European Journal of Cancer, vol. 41, (2005), pp. 1649-1654.
Oda, et al., High Frequency of Coexistent Mutants of PIK3CA and PTEN Genes in Endometrial Carcinoma. Cancer Research, (2005), vol. 65, No. 23, pp. 10669-10673.
Byun, et al., Frequent Monoatlelic Deletion PTEN and its Reciprocal Association With PIK3CA Amplification in Gastric Carcinoma. Int. J. Cancer, vol. 104, pp. 318-327, (2003).
Lee, et al., PIK3CA Gene is Frequently Mutated in Breast Carcinomas and Hepatocellular Carcinomas, Oncogene, (2005), vol. 24, pp. 1477-1480.
Tang, et al., Phosphorylated Akt Overexprossion and Lose of PTEN Expression in Non-Small Cell Lung Cancer Confers Poor Prognosis, Lung Cancer, (2006), vol. 51, pp. 181-191.
Wu, et al., Uncommon Mutation, But Common Amplifications, of the PIK3CA Gene in Thyroid Tumors, The Journal of Clinical Endocrinology & Metabolism. vol. 90, No. 8, pp. 4688-4693, (2005).
Sujobert, et al., Essential Role for the p1108 Isoform in Phosphoinositide 3-Kinase Activation and Cell Proliferation in Acute Myeloid Leukemia, Blood, vol. 106, No. 3, pp. 1063-1066, (2005).
Hartmann, et al., PIK3CA Mutations in Glioblastoma Multiforme Acta Neuropathol, (2005), vol. 109, pp. 639-642.
Bachman, et al., The PIK3CA Gene is Mutated With High Frequency in Human Breast Cancers, Cancer Biology & Therapy, vol. 3, No. 9, pp. 772-775. (2004).

(Continued)

*Primary Examiner* — Douglas M Willis
(74) *Attorney, Agent, or Firm* — Brian R. Morrill

(57) ABSTRACT

Provided herein are various polymorph forms of N-(3-{[(2Z)-3-[(2-chloro-5-methoxyphenyl)amino]quinoxalin-2(1H)-ylidene]sulfamoyl}phenyl)-2-methylalaninamide.

25 Claims, 23 Drawing Sheets

(56) References Cited

OTHER PUBLICATIONS

Samuels, et al., Oncogenic Mutations of PIK3CA in Human Cancers, Cell Cycle, vol. 3, No. 10, pp. e17-e19, (2004).

Massion, et al., Early Involvement of the Phosphatidylinositol 3-Kinase/Akt Pathway in Lung Cancer Progression, American Journal of Respiratory and Critical Care Medicine, vol. 170, pp. 1068-1094, (2004).

* cited by examiner

POLYMORPH OF N-(3-{[(2Z)-3-[(2-CHLORO-5-METHOXYPHENYL)AMINO]QUINOXALIN-2(1H)-YLIDENE]SULFAMOYL}PHENYL)-2-METHYLALANINAMIDE

CROSS-REFERENCE TO RELATED APPLICATIONS

This application is a continuation of International Application No. PCT/EP2013/069068 filed on Sep. 13, 2013 which claims priority to FR Application No. 1356284 filed on Jun. 28, 2013 and to U.S. Provisional Application No. 61/700,618 filed on Sep. 13, 2012.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

1. Field of the Invention

According to National Cancer Institute statistics, 41% of men and women alive today will be diagnosed with cancer at some point in their lives. The widespread occurrence of this disease underscores the need for improved anticancer regimens for the treatment of malignancy.

One important drug target is a group of proteins called kinases. Protein kinases are a large and diverse family of enzymes that catalyze protein phosphorylation and play a critical role in cellular signaling. They may exert positive or negative regulatory effects, depending upon their target protein. Protein kinases are involved in specific signaling pathways which regulate cell functions such as, but not limited to, metabolism, cell cycle progression, cell adhesion, vascular function, apoptosis, and angiogenesis. Malfunctions of cellular signaling have been associated with many diseases, the most characterized of which include cancer and diabetes. The regulation of signal transduction by cytokines and the association of signal molecules with proto-oncogenes and tumor suppressor genes have been well documented. Similarly, the connection between diabetes and related conditions, and deregulated levels of protein kinases, has been demonstrated. See e.g., Sridhar et al. Pharmaceutical Research, 17(11): 1345-1353 (2000). Viral infections and the conditions related thereto also have been associated with the regulation of protein kinases. Park et al. Cell 101 (7), 777-787 (2000).

Phosphatidylinositol 3-kinase (PI3K or PIK3CA) is composed of an 85 kDa regulatory subunit and a 110 kDa catalytic subunit. The protein encoded by this gene represents the catalytic subunit, which uses ATP to phosphorylate PtdIns, PtdIns4P and PtdIns(4,5)P2. PTEN, a tumor suppressor which inhibits cell growth through multiple mechanisms, can dephosphorylate PIP3, the major product of PIK3CA. PIP3, in turn, is required for translocation of protein kinase B (AKT1, PKB) to the cell membrane, where it is phosphorylated and activated by upstream kinases. The effect of PTEN on cell death is mediated through the PIK3CA/AKT1 pathway.

PI3Kα has been implicated in the control of cytoskeletal reorganization, apoptosis, vesicular trafficking, proliferation and differentiation processes. Increased copy number and expression of PIK3CA is associated with a number of malignancies such as ovarian cancer (Campbell et al., Cancer Res 2004, 64, 7678-7681; Levine et al., Clin Cancer Res 2005, 11, 2875-2878; Wang et al., Hum Mutat 2005, 25, 322; Lee et al., Gynecol Oncol 2005, 97, 26-34), cervical cancer, breast cancer (Bachman, et al. Cancer Biol Ther 2004, 3, 772-775; Li et al., Breast Cancer Res Treat 2006, 96, 91-95; Saal et al., Cancer Res 2005, 65, 2554-2559; Samuels and Velculescu, Cell Cycle 2004, 3, 1221-1224), colorectal cancer (Samuels, et al. Science 2004, 304, 554; Velho et al. Eur J Cancer 2005, 41, 1649-1654), endometrial cancer (Oda et al. Cancer Res. 2005, 65, 10669-10673), gastric carcinomas (Byun et al., Int J Cancer 2003, 104, 318-327; Lee et al., Oncogene 2005, 24, 1477-1480), hepatocellular carcinoma (Lee et al., Oncogene 2005, 24, 1477-1480), small and non-small cell lung cancer (Tang et al., Lung Cancer 2006, 51, 181-191; Massion et al., Am J Respir Crit Care Med 2004, 170, 1088-1094), thyroid carcinoma (Wu et al., J Clin Endocrinol Metab 2005, 90, 4688-4693), acute myelogenous leukemia (AML) (Sujobert et al., Blood 1997, 106, 1063-1066), chronic myelogenous leukemia (CML) (Hickey and Cotter J Biol Chem 2006, 281, 2441-2450), and glioblastomas (Hartmann et al. Acta Neuropathol (Berl) 2005, 109, 639-642).

A number of PI3K inhibitors are presently undergoing clinical evaluation in patients with cancer, the details of which can be reviewed at the web site ClinicalTrials.gov. For example, human clinical trials are underway to evaluate a form of N-(3-{[(2Z)-3-[(2-chloro-5-methoxyphenyl)amino]quinoxalin-2(1H)-ylidene]sulfamoyl}phenyl)-2-methylalaninamide in patients with lymphoma (See trial NCT00486135), non-small-cell lung cancer (See trial NCT00692640), endometrial cancer (See trials NCT01013324 and NCT00756847) breast cancer (See trials NCT01042925 and NCT01082068) or other solid tumor (See trials NCT01357330, NCT01390818 and NCT01436565). In light the compound's established biological activity, optimized forms are needed to achieve maximal patient efficacy.

2. Description of Related Art

Not Applicable

BRIEF SUMMARY OF THE INVENTION

Accordingly, there is provided, in one aspect, an isolated compound N-(3-{[(2Z)-3-[(2-chloro-5-methoxyphenyl)amino]quinoxalin-2(1H)-ylidene]sulfamoyl}phenyl)-2-methylalaninamide:

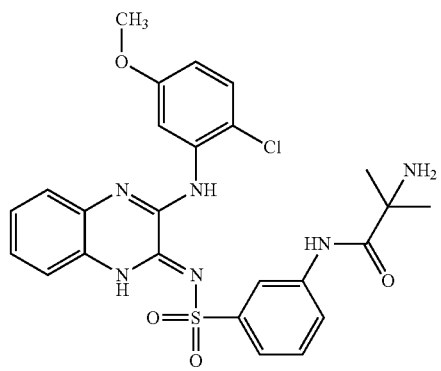 [SMILES: COc1ccc(Cl)c(Nc2nc3ccccc3[nH]/c2=N\S(=O)(=O)c2cccc(NC(=O)C(C)(C)N)c2)c1]

or a pharmaceutically acceptable salt or solvate thereof

Throughout the application, N-(3-{[(2Z)-3-[(2-chloro-5-methoxyphenyl)amino]quinoxalin-2(1H)-ylidene]sulfamoyl}phenyl)-2-methylalaninamide is referred to as "compound (I)."

In one aspect, provided herein is a pharmaceutical composition comprising compound (I), or a pharmaceutically acceptable salt or solvate thereof, and a pharmaceutically acceptable carrier, excipient, or diluent.

It has been found that solid forms of compound (I) can be prepared as one or more polymorph forms, including hydrate and solvate forms. These polymorph forms exhibit new physical properties that can be exploited in order to obtain new pharmacological properties, and that may be utilized in drug substance and drug product development. Accordingly, in one aspect, provided herein is polymorph E of the compound N-(3-{[(2Z)-3-[(2-chloro-5-methoxyphenyl)amino]quinoxalin-2(1H)-ylidene]sulfamoyl}phenyl)-2-methylalaninamide.

In certain aspects, provided herein are solvate forms of compound (I), including a AcOBut (butyl acetate) solvate, a THF (tetrahydrofuran) solvate, a mixed DMAC (dimethylacetamide)/Toluene solvate, and a DMSO (dimethylsulfoxide) solvate.

In another aspect, provided herein is a pharmaceutical composition comprising polymorph E of compound (I), and a pharmaceutically acceptable carrier or diluent.

In still another aspect, provided herein is a process for the preparation of polymorph E of compound (I), which comprises the following steps: (a) dissolving compound (I) in a first solvent, (b) optionally adding a second solvent, and (e) optionally seeding the mixture, such that said polymorph is formed.

In another aspect, provided herein is a method of treating cancer in a subject comprising administering to the subject compound (I) or a pharmaceutical composition comprising compound (I).

In another aspect, provided herein is a method of treating cancer in a subject comprising administering to the subject polymorph E or a pharmaceutical composition comprising polymorph E.

In one embodiment of the above methods, the cancer is a solid tumor. In another embodiment, the cancer is breast cancer, colon cancer, rectal cancer, endometrial cancer, gastric carcinoma, glioblastoma, hepatocellular carcinoma, small cell lung cancer, non-small cell lung cancer, melanoma, ovarian cancer, cervical cancer, pancreatic cancer, prostate carcinoma, acute myelogenous leukemia (AML), chronic myelogenous leukemia (CML), or thyroid carcinoma.

In still another embodiment, the cancer is endometrial cancer, ovarian cancer, cervical cancer, breast cancer, colon cancer, rectal cancer, or glioblastoma. In still another embodiment, the cancer is endometrial cancer, ovarian cancer, non-small cell lung cancer (NSCLC), breast cancer, or lymphoma. The treatments can comprise the administration of an additional anticancer agent. Non-limiting examples of such agents include carboplatin, paclitaxel, erlotinib and trastuzumab.

Also provided herein is the use of compound (I) (e.g., polymorph E) in the manufacture of a medicament for treating cancer in a subject.

In another aspect, methods are provided for treating disorders mediated by PI3K, comprising administering to a subject in need of such treatment an effective amount of compound (I) (e.g., polymorph E) or a pharmaceutical composition comprising compound (I) (e.g., polymorph E). In an embodiment, the disorder mediated by PI3K is cancer. Non-limiting cancers that can be treated are breast cancer, colon cancer, rectal cancer, endometrial cancer, gastric carcinoma, glioblastoma, hepatocellular carcinoma, small cell lung cancer, non-small cell lung cancer, melanoma, ovarian cancer, cervical cancer, pancreatic cancer, prostate carcinoma, acute myelogenous leukemia (AML), chronic myelogenous leukemia (CML), or thyroid carcinoma.

Also provided is the use of compound (I) (e.g., polymorph E) for the preparation of a medicament for the treatment of disorders mediated by PI3K.

In another aspect, provided herein is a method of inhibiting the activity of PI3K kinase comprising utilizing compound (I) (e.g., polymorph E).

In another embodiment, kits are provided comprising polymorph E of the compound N-(3-{[(2Z)-3-[(2-chloro-5-methoxyphenyl)amino]quinoxalin-2(1H)-ylidene]sulfamoyl}phenyl)-2-methylalaninamide. In one example, the kit contains a pharmaceutical composition comprising polymorph E of N-(3-{[(2Z)-3-[(2-chloro-5-methoxyphenyl)amino]quinoxalin-2(1H)-ylidene]sulfamoyl}phenyl)-2-methylalaninamide. In one embodiment, the kit comprises instructions for using the compound or pharmaceutical composition to treat a patient with cancer.

Other objects, features and advantages will become apparent from the following detailed description. The detailed description and specific examples are given for illustration only since various changes and modifications within the spirit and scope of the invention will become apparent to those skilled in the art from this detailed description. Further, the examples demonstrate the principle of the invention and cannot be expected to specifically illustrate the application of this invention to all the examples where it will be obviously useful to those skilled in the art.

DETAILED DESCRIPTION OF THE INVENTION

Figure 1:
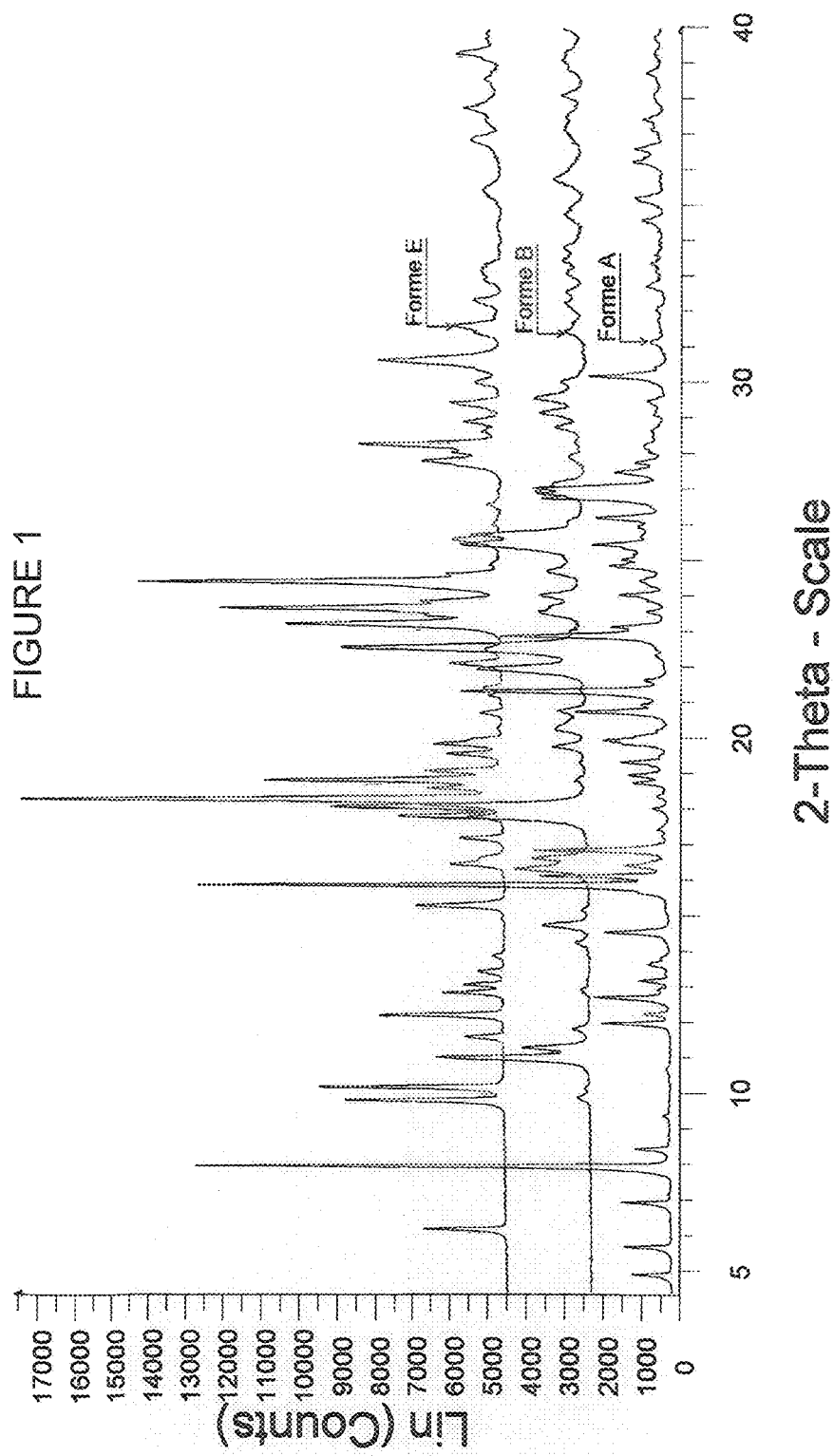
FIG. 1 depicts the X-ray powder diffraction pattern of polymorph E, as well as polymorph A and pseudo-polymorph B (sesquihydrate).

Isolated N-(3-{[(2Z)-3-[(2-chloro-5-methoxyphenyl)amino]quinoxalin-2(1H)-ylidene]sulfamoyl}phenyl)-2-methylalaninamide is provided along with methods of making and using the same. Crystalline forms of N-(3-{[(2Z)-3-[(2-chloro-5-methoxyphenyl)amino]quinoxalin-2(1H)-ylidene]sulfamoyl}phenyl)-2-methylalaninamide also are provided, as well as pharmaceutical compositions comprising same and methods for their use.

Compound (I)

Accordingly, provided herein is the isolated compound N-(3-{[(2Z)-3-[(2-chloro-5-methoxyphenyl)amino]quinoxalin-2(1H)-ylidene]sulfamoyl}phenyl)-2-methylalaninamide:

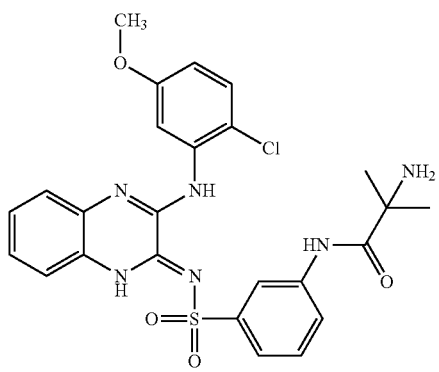 [SMILES: COc1ccc(Cl)c(Nc2nc3ccccc3[nH]/c2=N\S(=O)(=O)c2cccc(NC(=O)C(C)(C)N)c2)c1]

or a pharmaceutically acceptable salt or solvate thereof. This compound can be used to inhibit and/or modulate PI3Kα in biological processes, and is therefore useful for the treatment of related disease states.

Throughout the application, N-(3-{[(2Z)-3-[(2-chloro-5-methoxyphenyl)amino]quinoxalin-2(1H)-ylidene]sulfamoyl}phenyl)-2-methylalaninamide, or a pharmaceutically acceptable salt or solvate thereof, is referred to as "compound (I)." It will be recognized that N-(3-{[(2Z)-3-[(2-chloro-5-methoxyphenyl)amino]quinoxalin-2(1H)-ylidene]sulfamoyl}phenyl)-2-methylalaninamide may exist in alternate tautomeric forms. One example is N-(3-{[(3-{[2-chloro-5-(methoxy)phenyl]amino}quinoxalin-2-yl)amino]sulfonyl}phenyl)-2-methylalaninamide,

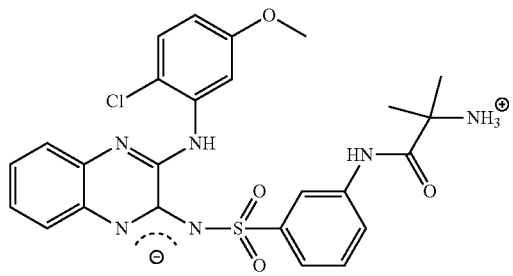 [SMILES: COc1ccc(Cl)c(NC2=Nc3ccccc3NC2NS(=O)(=O)c2cccc(NC(=O)C(C)(C)[NH3+])c2)c1]

In another example, the compound may exist, for instance in solution, as a zwitterion, such as In one aspect, isolated N-(3-{[(2Z)-3-[(2-chloro-5-methoxyphenyl)amino]quinoxalin-2(1H)-ylidene]sulfamoyl}phenyl)-2-methylalaninamide is provided comprising less than 10%, less than 5, less than 1% or less than 0.1% N-(3-{[(3-{[2-chloro-5-(methoxy)phenyl]amino}quinoxalin-2-yl)amino]sulfonyl}phenyl)-2-methylalaninamide.

Also provided herein are prodrug forms of this compound, as well as non-salt and non-solvate forms of this compound.

Pharmaceutically acceptable salts for Compound (I) include, for example, hydrochloride, sulfate (i.e., sulphate), mesylate, besylate, 2-hydroxyethane sulphonate, maleate, glutamate, malonate, 2,5-dihydroxybenzoate, tartrate, and fumarate salts, as well as potassium, arginine, calcium, magnesium and lysine salts. In some embodiments, the pharmaceutically acceptable salt is selected from the group consisting of mono-maleate, fumarate and hydrochloride salts.

"Prodrug" refers to compounds that are transformed (typically rapidly) in vivo to yield the active ingredient of the above formulae, for example, by hydrolysis in blood. Common examples of a prodrug include, but are not limited to, amide forms of a compound having an active form bearing a carboxylic acid or an amine moiety.

Examples of pharmaceutically acceptable amides of the compounds of this invention include, but are not limited to, primary amides, and secondary and tertiary alkyl amides (for example with between about one and about six carbons).

The term "isolated" denotes that a compound is substantially separated from the environment in which it was formed. Substantial separation can include compositions containing at least about 80%, at least about 90%, at least about 95%, at least about 97%, or at least about 99% by weight of the compound.

In another aspect, the product of the synthetic process described in Example 1 is provided. As the product is a potent PI3K inhibitor, it is useful for treating disorders mediated by PI3K, such as cancer. In one embodiment, pharmaceutical compositions are provided comprising the product.

Polymorph Forms and Properties

Provided herein are crystalline forms of N-(3-{[(2Z)-3-[(2-chloro-5-methoxyphenyl)amino]quinoxalin-2(1H)-ylidene]sulfamoyl}phenyl)-2-methylalaninamide, which is referred to herein as "compound (I)". Accordingly, crystalline forms of compound (I), and pharmaceutical compositions comprising crystalline forms of compound (I), can be used for the prevention, amelioration or treatment of diseases depending on PI3K. As described herein, the free base of compound (I) can be a crystalline form that exists as one or more polymorphs, including hydrate and solvate forms. Polymorphs of compound (I) referred to herein include polymorph A, pseudo-polymorph B, and polymorph E. In a particular embodiment, provided herein is a polymorph form E of compound (I). In general, polymorphs (alternatively known in the art as polymorph forms, polymorphic forms or crystal forms) differ with respect to their X-ray powder diffraction patterns, spectroscopic, physicochemical and pharmacokinetic properties, as well as their thermodynamic stability.

The ability of a substance to exist in more than one crystal form is defined as polymorphism; the different crystal forms of a particular substance are referred to as "polymorphs." In general, polymorphism is affected by the ability of a molecule of a substance to change its conformation or to form different intermolecular or intra-molecular interactions, particularly hydrogen bonds, which is reflected in different atom arrangements in the crystal lattices of different polymorphs. In contrast, the overall external form of a substance is known as "morphology," which refers to the external shape of the crystal and the planes present, without reference to the internal structure. Crystals can display different morphology based on different conditions, such as, for example, growth rate, stirring, and the presence of impurities.

The different polymorphs of a substance may possess different energies of the crystal lattice and, thus, in solid state they may show different physical properties such as form, density, melting point, color, stability, solubility, dissolution rate, etc., which may, in turn, affect the stability, dissolution rate and/or bioavailability of a given polymorph and its suitability for use as a pharmaceutical and in pharmaceutical compositions.

When polymorphism exists as a result of difference in crystal packing, it is called packing polymorphism. In pseudo-polymorphism the different crystal types are the result of hydration or solvation. The term "pseudo-polymorph" may be used in reference to a crystalline form of a compound that is constitutionally different than the compound of a corresponding "polymorph". For example, a crystalline form of a sesquihydrate of compound (I) may be referred to as a "pseudo-polymorph".

Access to different polymorphs of compound (I) is desirable for a number of reasons. One such reason is that individual polymorphs may incorporate different impurities, or chemical residues, upon crystallization. Thus, the sequential preparation of different polymorphs of compound (I) may be used to increase the purity of the compound. For example, impurities can be removed during the process of converting raw compound (I) into polymorph A or polymorph E.

In certain embodiments, certain solvates of compound (I) are provided herein. The term "solvate" refers to any form of compound (I) that is bound by a non-covalent bond to another molecule (such as a polar solvent). Such solvates are typically crystalline solids having a substantially fixed molar ratio of solute and solvent. Representative solvents include THF, DMSO, DMAC and butyl acetate (AcOBut). When the solvent is water, the solvate formed is a hydrate.

In certain embodiments of the processes described herein, intermediate solvate forms of compound (I) are obtained by exposing the compound to sequential solvents. For example, compound (I) may be exposed to THF, thereby producing a THF-solvate. The THF-solvate may be subsequently exposed to a different solvent, thereby forming a different solvate of polymorph of compound (I). Sequential formation of solvates and/or polymorphs may promote a purification effect.

Accordingly, in an embodiment, compound (I) is exposed to butyl acetate, thereby producing a AcOBut-solvate (also referred to herein as "Solvate C"). In another embodiment, compound (I) is exposed to THF, thereby producing a THF-solvate (also referred to herein as "Solvate D"). In yet another embodiment, compound (I) is exposed to DMAC, thereby producing a DMAC-solvate. In still another embodiment, compound (I) is exposed to DMSO, thereby producing a DMSO-solvate.

In another embodiment, compound (I) is exposed to DMAC and toluene, thereby producing a mixed DMAC/toluene solvate (also referred to as a toluene/DMAC solvate). Accordingly, provided herein is a toluene/DMAC mixed solvate of compound (I). The toluene/DMAC mixed solvate can contain 2 molecules of DMAC and 1 molecule of toluene per 1 molecule of compound (I).

In another embodiment, provided herein is a DMSO-solvate of compound (I) containing one molecule of DMSO per one molecule of compound (I).

In an embodiment, either of the DMSO-solvate of compound (I) or DMAC-solvate or mixed DMAC/toluene solvate of compound (I) can be exposed to a solvent, such as ethanol, to form Polymorph E.

Accordingly, a particular polymorph may represent the most suitable form for a given application, including, but not limited to, use as an intermediate in a manufacturing process, or in particular administration forms such as suspensions, emulsions, solutions, ointments, tablets or capsules, or in the manufacture of a drug form having preferred pharmacokinetic properties.

Without wishing to be bound by theory, polymorph forms exhibiting compact crystal shapes possess advantages in terms of ease of filtration and ease of flow. Polymorph E exhibits a compact crystal shape that therefore possesses these advantages.

Thus, in one aspect, provided herein is a crystalline form of compound (I), or a hydrate, solvate, or salt thereof.

In another aspect, provided herein is polymorph E of compound (I), also referred to herein as "polymorph E".

In certain embodiments, polymorph E is identifiable on the basis of characteristic peaks in an X-ray powder diffraction analysis. X-ray powder diffraction, also referred to as XRPD, is a scientific technique using X-ray, neutron, or electron diffraction on powder, microcrystalline, or other solid materials for structural characterization of the materials. In one embodiment, polymorph E exhibits an X-ray powder diffraction pattern having characteristic peaks expressed in degrees 2-Theta at angles of 18.3°±0.3° and 24.4°±0.3°. In another embodiment, polymorph E exhibits characteristic peaks at angles of 18.8°±0.3° and 23.7°±0.3°. In another embodiment, polymorph E exhibits characteristic peaks at angles of 9.8°±0.3° and 23.2°±0.3°. In another embodiment, polymorph E exhibits characteristic peaks at angles of 10.1°±0.3° and 28.3°±0.3°. In another embodiment, polymorph E exhibits characteristic peaks at angles of 9.8°±0.3°, 10.1°±0.3°, 18.3°±0.3°, 18.8°±0.3°, 23.2°±0.3°, 23.7°±0.3° 28.3°±0.3° and 24.4°±0.3°. In still another embodiment, polymorph E exhibits an X-ray powder diffraction pattern that possesses two or more characteristic peaks (±0.3°) listed in Table 1. In yet another embodiment, polymorph E exhibits an X-ray powder diffraction pattern substantially in accordance with FIG. 1 or Table 1, or both FIG. 1 and Table 1.

Pharmaceutical compositions comprising polymorph E can be identified by comparison of the compositions' X-ray powder diffraction patterns to an X-ray powder diffraction pattern of pure polymorph E. It will be appreciated that pharmaceutical compositions comprising polymorph E may exhibit non-identical X-ray powder diffraction patterns as compared to an X-ray powder diffraction pattern of pure polymorph E.

In other embodiments, polymorph E is identifiable on the basis of characteristic peaks in an FT-IR spectrum. FT-IR, also referred to as Fourier transform infrared spectroscopy, is a technique which is used to obtain an infrared spectrum of absorption, emission, photoconductivity or Raman scattering of a material. In one embodiment, polymorph E exhibits an FT-IR spectrum having characteristic peaks expressed in units of $cm^{-1}$ at values of about 1682, about 1296 and about 1136. In another embodiment, polymorph E exhibits an FT-IR spectrum that possesses two or more characteristic peaks (±4 $cm^{-1}$) listed in Table 2. In another embodiment, polymorph E exhibits an FT-IR spectrum substantially in accordance with FIG. 2.

Pharmaceutical compositions comprising polymorph E may be identified by comparison of the compositions' FT-IR spectra to an FT-IR spectrum of pure polymorph E. It will be appreciated that compositions comprising polymorph E may exhibit non-identical FT-IR spectra as compared to an FT-IR spectrum of pure polymorph E.

Figure 3:
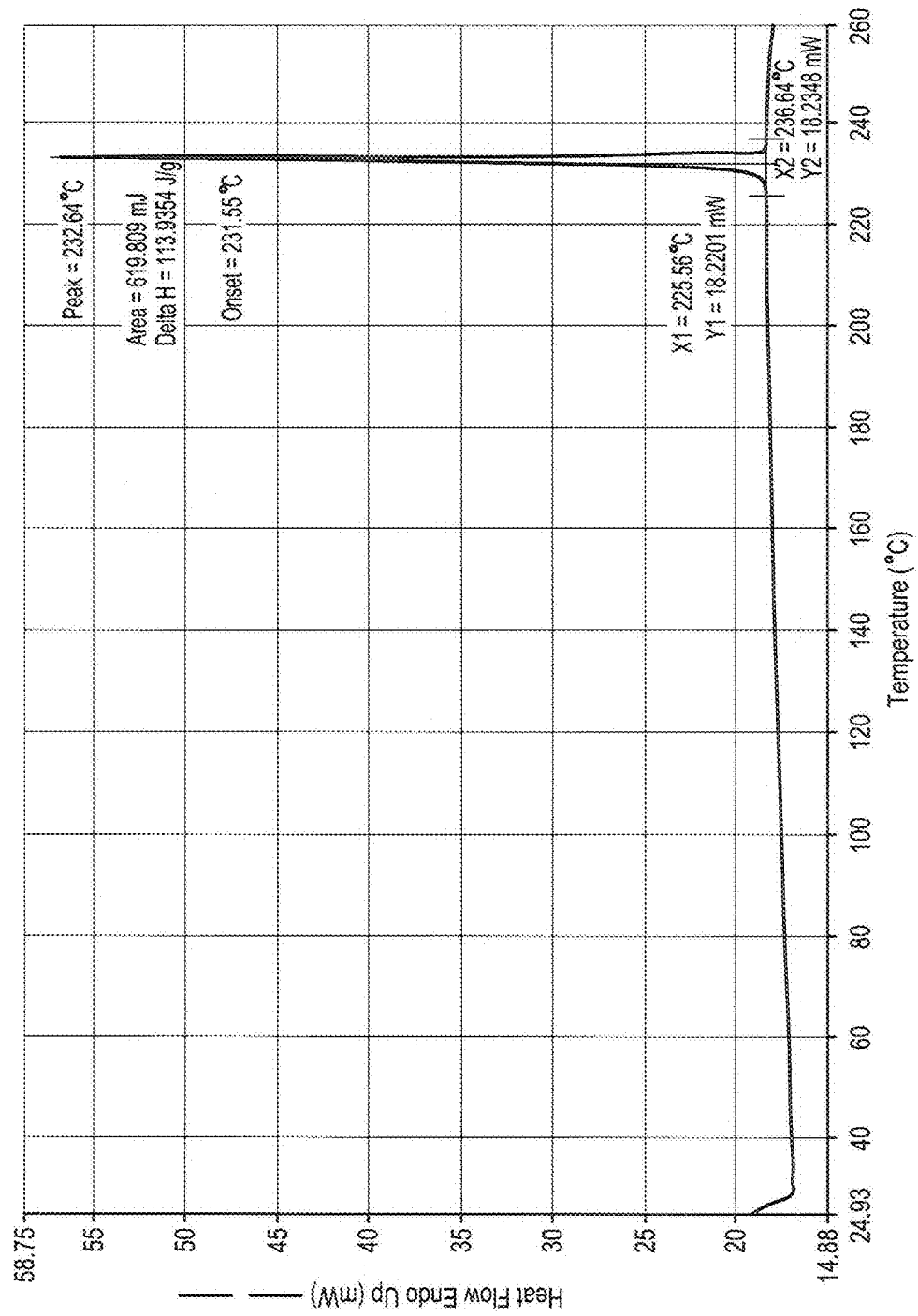
FIG. 3 depicts the differential scanning calorimetry thermogram of polymorph E.

In other embodiments, polymorph E is identifiable on the basis of a characteristic peak observed in a differential scanning calorimetry thermogram. Differential scanning calorimetry, or DSC, is a thermoanalytical technique in which the difference in the amount of heat required to increase the temperature of a sample and reference is measured as a function of temperature. In one embodiment, polymorph E exhibits a differential scanning calorimetry thermogram having a characteristic peak expressed in units of ° C. at a temperature of about 232±2° C. (e.g., 232.6±2° C.). In another embodiment, polymorph E exhibits a differential scanning calorimetry thermogram substantially in accordance with FIG. 3.

Figure 4:
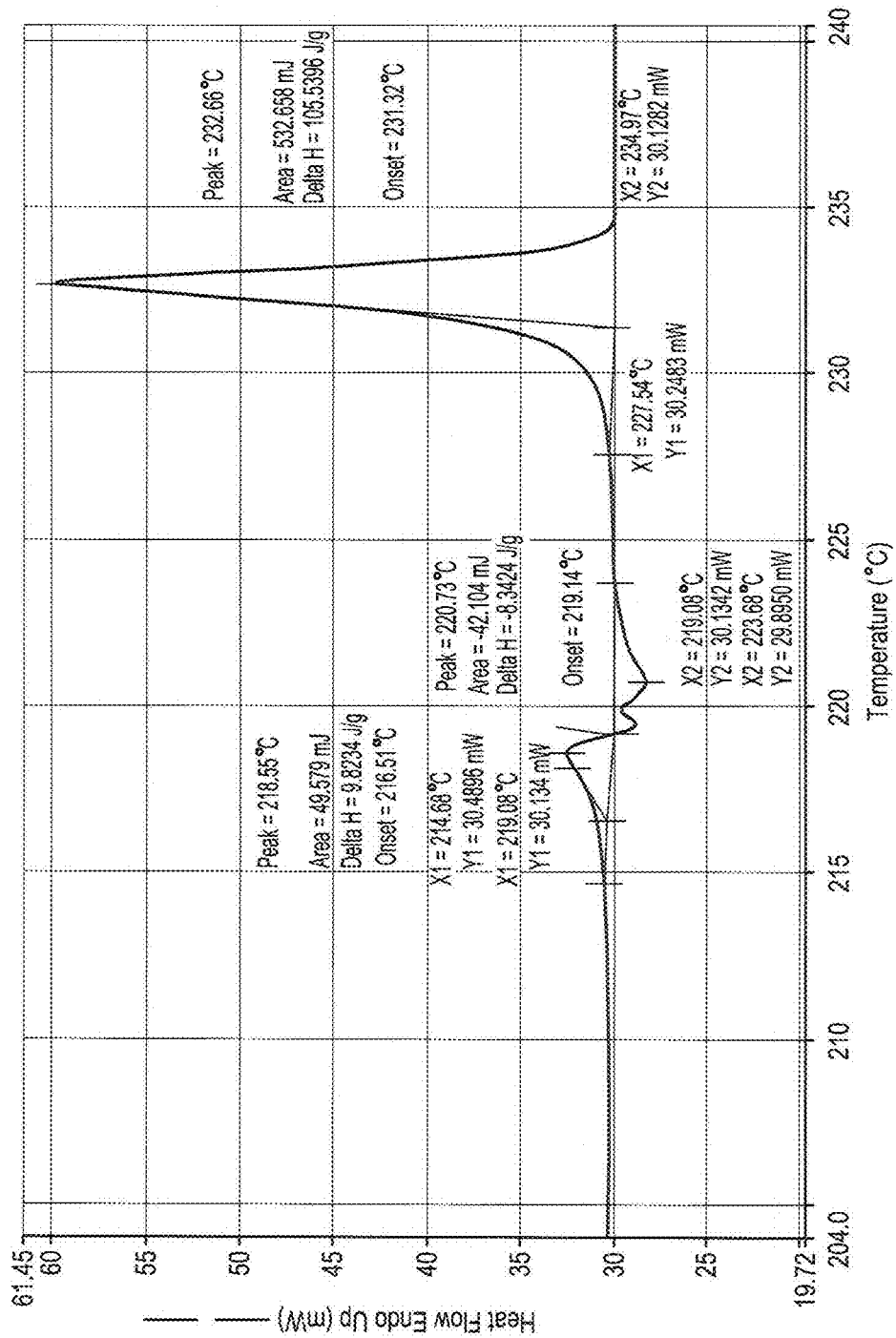
FIG. 4 depicts the differential scanning calorimetry thermogram of a 50/50 (w/w) solid mixture of polymorphs E and A.

In other embodiments, an approximate 50/50 (w/w) solid mixture of polymorphs E and A is identifiable on the basis of a characteristic peak observed in a differential scanning calorimetry thermogram. In one embodiment, an approximate 50/50 (w/w) solid mixture of polymorphs E and A exhibits a differential scanning calorimetry thermogram having a characteristic peak expressed in units of ° C. with an onset temperature of abut about 231, e.g., 231.3 and a peak at about 232, e.g., 232.7. In another embodiment, an approximate 50/50 (w/w) solid mixture of polymorphs E and A exhibits a differential scanning calorimetry thermogram substantially in accordance with FIG. 4.

In another embodiment, polymorph E exhibits a melting point expressed in units of ° C. at a temperature in the range of about 230-235. In one embodiment, polymorph E exhibits a melting point expressed in units of ° C. at a temperature in the rage of about 231-233. In certain embodiments, polymorph E has an enthalpy of fusion of about 114 J/g.

Figure 5:
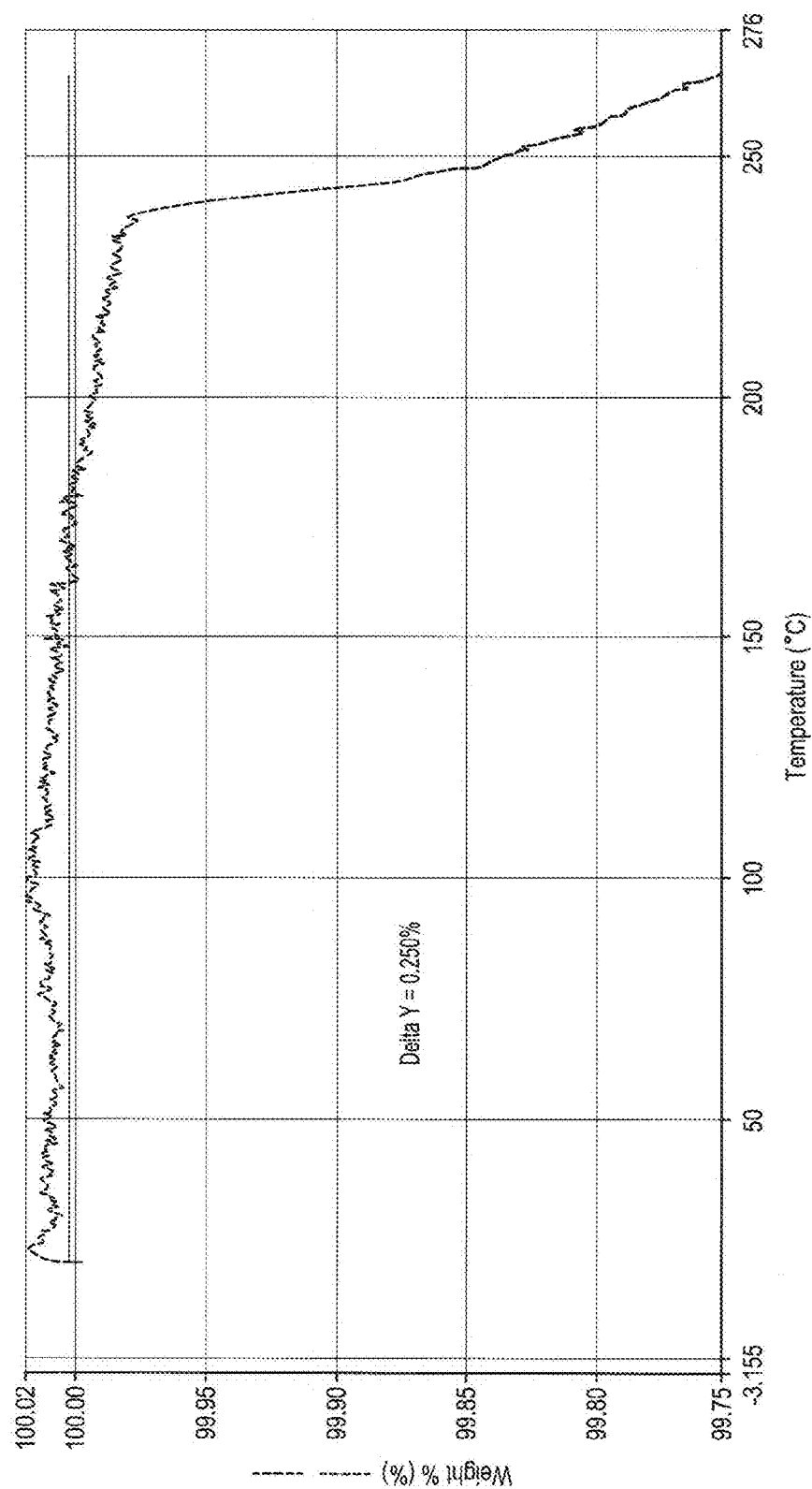
FIG. 5 depicts results of a thermogravimetric analysis of polymorph E. Thermogravimetric analysis was performed using a Perkin Elmer 1 analyzer at 5° C./min.

In some embodiments, polymorph E is identifiable on the basis of a characteristic thermogravimetry curve. Thermogravimetry, also referred to as TG, involves analysis (i.e., thermogravimetric analysis) based on a continuous recording of mass changes of a sample of material as a function of a combination of temperature, time, and in some instances pressure. In one embodiment, polymorph E exhibits a thermogravimetry curve substantially in accordance with FIG. 5.

In other embodiments, polymorph E may contain impurities. Non-limiting examples of impurities include undesired polymorph forms, or residual organic and inorganic molecules such as solvents, water or salts. In one embodiment, polymorph E contains less than 10% by weight total impurities. In another embodiment, polymorph E contains less than 5% by weight total impurities. In another embodiment, polymorph E contains less than 1% by weight total impurities. In yet another embodiment, polymorph E contains less than 0.1% by weight total impurities. In still another embodiment, polymorph E is substantially free from impurities.

In a particular embodiment, polymorph E is substantially free from polymorph A. In another embodiment, polymorph E is substantially free from pseudo-polymorph B.

In another aspect, provided herein is polymorph A of compound (I), also referred to herein as "polymorph A". In certain embodiments, polymorph A is identifiable on the basis of characteristic peaks in an X-ray powder diffraction analysis. In one embodiment, polymorph A exhibits an X-ray powder diffraction pattern having characteristic peaks expressed in degrees 2-Theta at angles of 10.9°±0.3° and 22.5°±0.3°. In another embodiment, polymorph A exhibits characteristic peaks at angles of 18.0°±0.3° and 11.2°±0.3°. In another embodiment, polymorph A exhibits characteristic peaks at angles of 17.8°±0.3° and 25.7°±0.3°. In another embodiment, polymorph A exhibits characteristic peaks at angles of 16.3°±0.3° and 21.9°±0.3°. In another embodiment, polymorph A exhibits characteristic peaks at angles of 10.9°±0.3°, 22.5°±0.3°, 18.0°±0.3°, 11.2°±0.3°, 17.8°±0.3°, 25.7°±0.3°, 16.3°±0.3° and 21.9°±0.3°. In still another embodiment, polymorph A exhibits an X-ray powder diffraction pattern that possesses two or more characteristic peaks (±0.3°) listed in Table 1. In yet another embodiment, polymorph A exhibits an X-ray powder diffraction pattern substantially in accordance with FIG. 17 or Table 5, or both FIG. 17 and Table 5.

Pharmaceutical compositions comprising polymorph A can be identified by comparison of the compositions' X-ray powder diffraction patterns to an X-ray powder diffraction pattern of pure polymorph A. It will be appreciated that pharmaceutical compositions comprising polymorph A may exhibit non-identical X-ray powder diffraction patterns as compared to an X-ray powder diffraction pattern of pure polymorph A.

In other embodiments, polymorph A is identifiable on the basis of characteristic peaks in an FT-IR spectrum. In one embodiment, polymorph A exhibits an FT-IR spectrum having characteristic peaks expressed in units of cm-1 at values of about 1627, about 1571 and about 833. In another embodiment, polymorph A exhibits an FT-IR spectrum that possesses two or more characteristic peaks (±4 cm-1) listed in Table 6. In another embodiment, polymorph A exhibits an FT-IR spectrum substantially in accordance with FIG. 18.

Pharmaceutical compositions comprising polymorph A may be identified by comparison of the compositions' FT-IR spectra to an FT-IR spectrum of pure polymorph A. It will be appreciated that compositions comprising polymorph A may exhibit non-identical FT-IR spectra as compared to an FT-IR spectrum of pure polymorph A.

Figure 19:
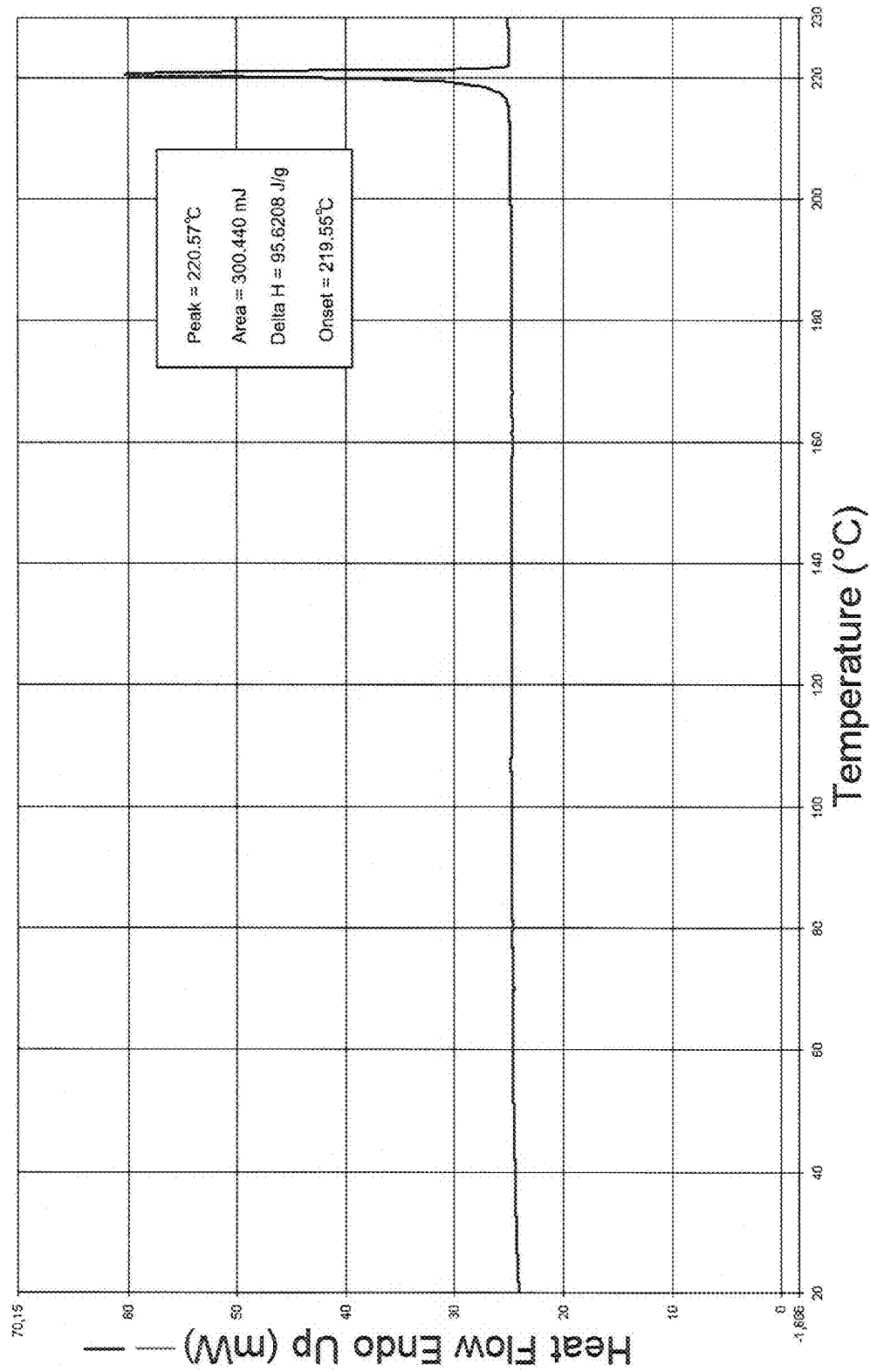
FIG. 19 depicts the differential scanning calorimetry thermogram of polymorph A.

In other embodiments, polymorph A is identifiable on the basis of a characteristic peak observed in a differential scanning calorimetry thermogram. In one embodiment, polymorph A exhibits a differential scanning calorimetry thermogram having a characteristic peak expressed in units of ° C. at a temperature of about 221±2° C. (e.g., 220.6±2° C.). In another embodiment, polymorph A exhibits a differential scanning calorimetry thermogram substantially in accordance with FIG. 19.

In another embodiment, polymorph A exhibits a melting point expressed in units of ° C. at a temperature in the range of about 218-223. In one embodiment, polymorph A exhibits a melting point expressed in units of ° C. at a temperature in the rage of about 219.5-221.5. In certain embodiments, polymorph A has an enthalpy of fusion of about 96 J/g.

Figure 20:
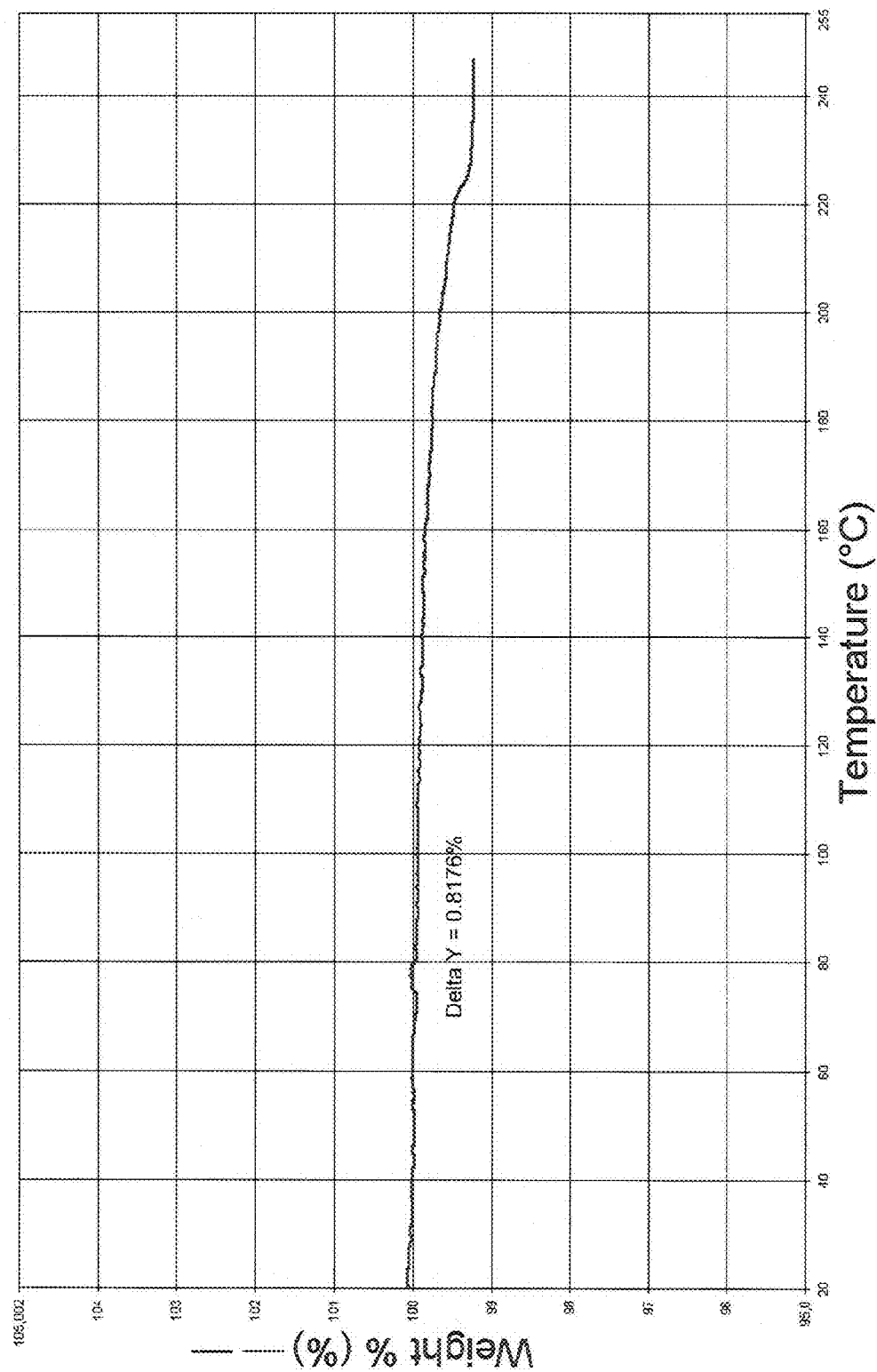
FIG. 20 depicts results of a thermogravimetric analysis of polymorph A.

In some embodiments, polymorph A is identifiable on the basis of a characteristic thermogravimetry curve. In one embodiment, polymorph A exhibits a thermogravimetry curve substantially in accordance with FIG. 20.

In another aspect, provided herein is pseudo-polymorph B of compound (I), also referred to herein as "pseudo-polymorph B". In certain embodiments, pseudo-polymorph B is identifiable on the basis of characteristic peaks in an X-ray powder diffraction analysis. In one embodiment, pseudo-polymorph B exhibits an X-ray powder diffraction pattern having characteristic peaks expressed in degrees 2-Theta at angles of 8.0°±0.3° and 15.9°±0.3°. In another embodiment, pseudo-polymorph B exhibits characteristic peaks at angles of 21.4°±0.3° and 16.9°±0.3°. In another embodiment, pseudo-polymorph B exhibits characteristic peaks at angles of 22.9°±0.3° and 16.2°±0.3°. In another embodiment, pseudo-polymorph B exhibits characteristic peaks at angles of 12.7°±0.3° and 20.8°±0.3°. In another embodiment, pseudo-polymorph B exhibits characteristic peaks at angles of 8.0°±0.3°, 12.7°±0.3°, 15.9°±0.3°, 16.2°±0.3°, 16.9°±0.3°, 20.8°±0.3°, 21.4°±0.3° and 22.9°±0.3°. In still another embodiment, pseudo-polymorph B exhibits an X-ray powder diffraction pattern that possesses two or more characteristic peaks (±0.3°) listed in Table 7. In yet another embodiment, pseudo-polymorph B exhibits an X-ray powder diffraction pattern substantially in accordance with FIG. 21 or Table 7, or both FIG. 21 and Table 7.

Pharmaceutical compositions comprising pseudo-polymorph B can be identified by comparison of the compositions' X-ray powder diffraction patterns to an X-ray powder diffraction pattern of pure pseudo-polymorph B. It will be appreciated that pharmaceutical compositions comprising pseudo-polymorph B may exhibit non-identical X-ray powder diffraction patterns as compared to an X-ray powder diffraction pattern of pure pseudo-polymorph B.

In other embodiments, pseudo-polymorph B is identifiable on the basis of characteristic peaks in an FT-IR spectrum. In one embodiment, pseudo-polymorph B exhibits an FT-IR spectrum having characteristic peaks expressed in units of cm-1 at values of about 1430, about 1336, about 1186, about 1011, about 992 and about 901. In another embodiment, pseudo-polymorph B exhibits an FT-IR spectrum that possesses two or more characteristic peaks (±4 cm-1) listed in Table 8. In another embodiment, pseudo-polymorph B exhibits an FT-IR spectrum substantially in accordance with FIG. 22.

Pharmaceutical compositions comprising pseudo-polymorph B may be identified by comparison of the compositions' FT-IR spectra to an FT-IR spectrum of pure pseudo-polymorph B. It will be appreciated that compositions comprising pseudo-polymorph B may exhibit non-identical FT-IR spectra as compared to an FT-IR spectrum of pure pseudo-polymorph B.

In other embodiments, pseudo-polymorph B is identifiable on the basis of a characteristic peak observed in a differential scanning calorimetry thermogram. In one embodiment, pseudo-polymorph B exhibits a differential scanning calorimetry thermogram having a characteristic peaks expressed in units of ° C. at a temperature of about 122±2° C. (e.g., 122.4±2° C.) and 133±2° C. (e.g., 132.8±2° C.) and 137±2° C. (e.g., 137.2±2° C.) and 219±2° C. (e.g., 219.1±2° C.) and 222±2° C. (e.g., 222.5±2° C.) and 234±2° C. (e.g., 233.6±2° C.).

In another embodiment, pseudo-polymorph B exhibits a dehydration point expressed in units of ° C. at a temperature in the range of about 120-125° C. In one embodiment, pseudo-polymorph B exhibits a dehydration point expressed in units of ° C. at a temperature in the rage of about 121-123.

Figure 23:
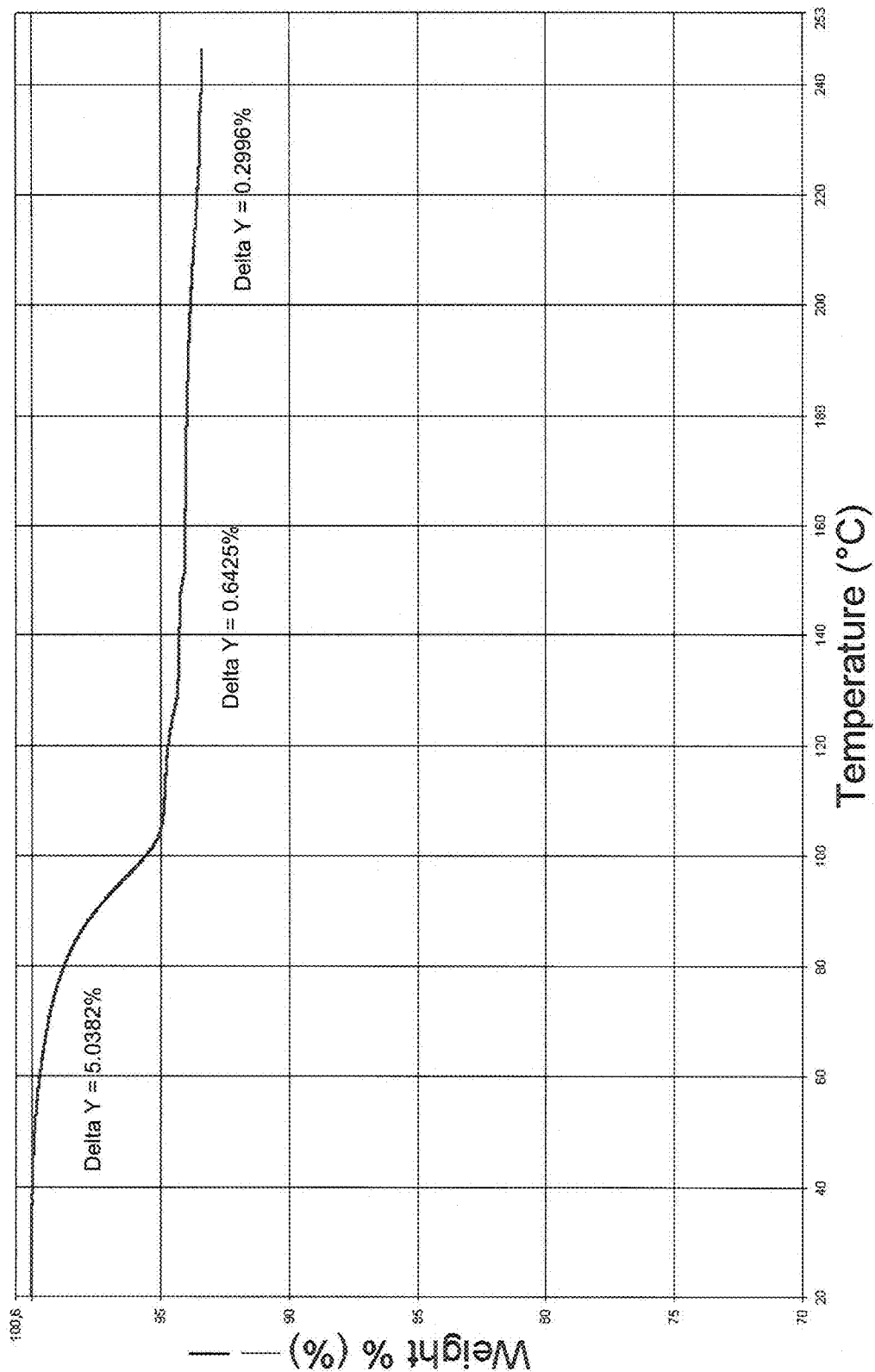
FIG. 23 depicts results of a thermogravimetric analysis of pseudo-polymorph B.

In some embodiments, pseudo-polymorph B is identifiable on the basis of a characteristic thermogravimetry curve. In one embodiment, pseudo-polymorph B exhibits a thermogravimetry curve substantially in accordance with FIG. 23.

Mixed DMAC/Toluene Solvate and DMSO Solvate of Compound (I)

Figure 11:
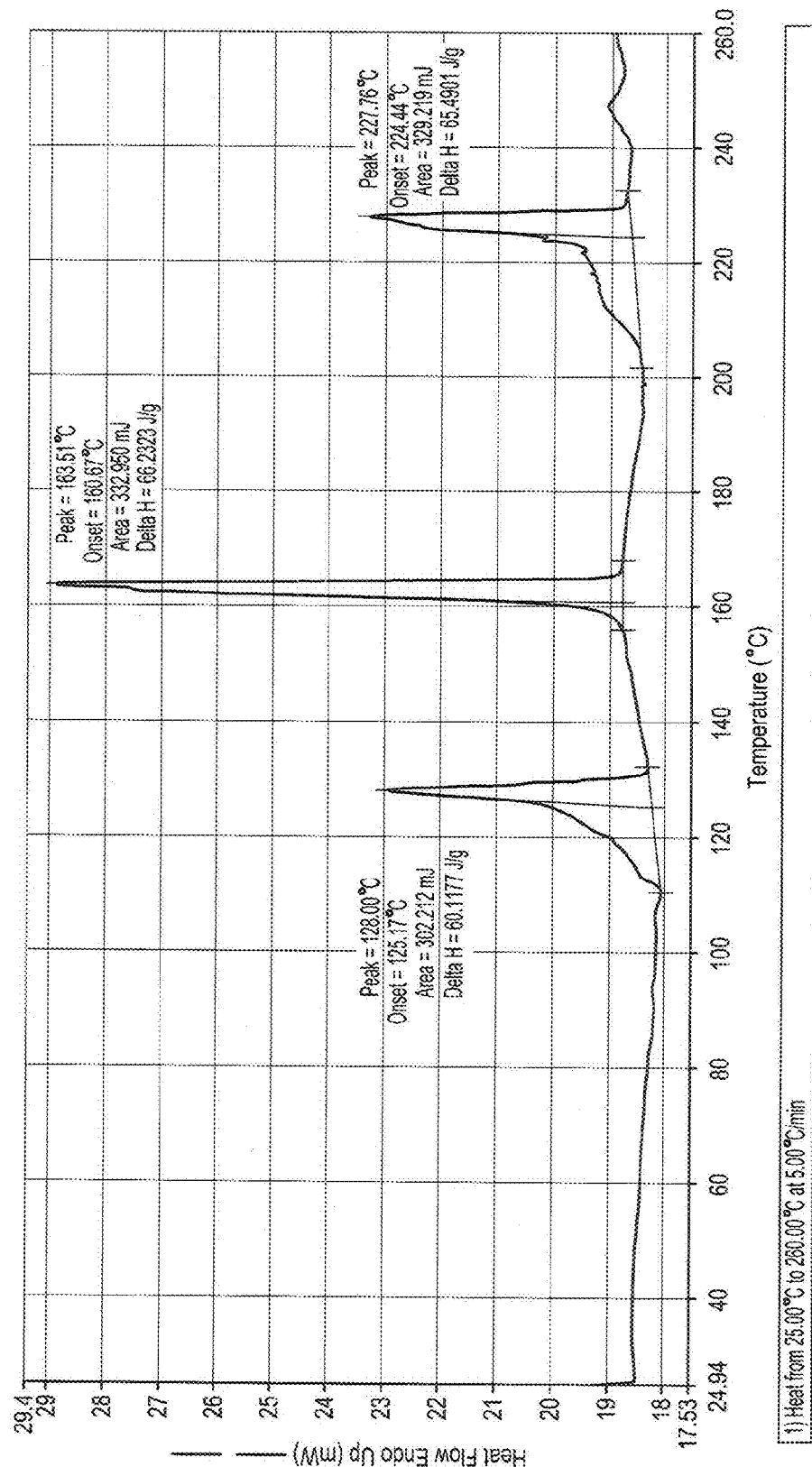
FIGS. 11-13 show DSC, TGA, and XRPD spectra for the mixed DMAC/toluene solvate of compound (I) provided herein.
Figure 12:
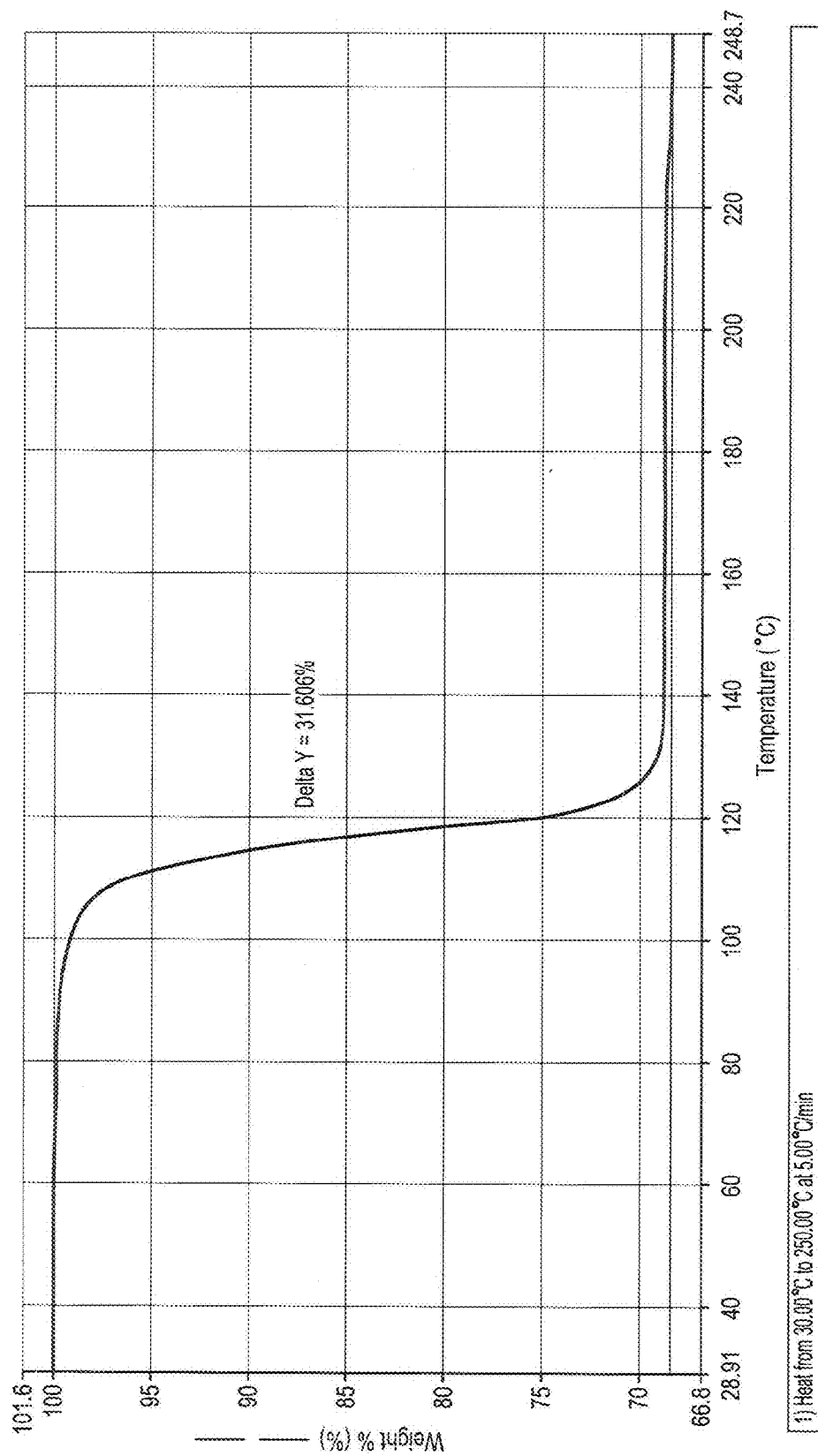
Figure 13:
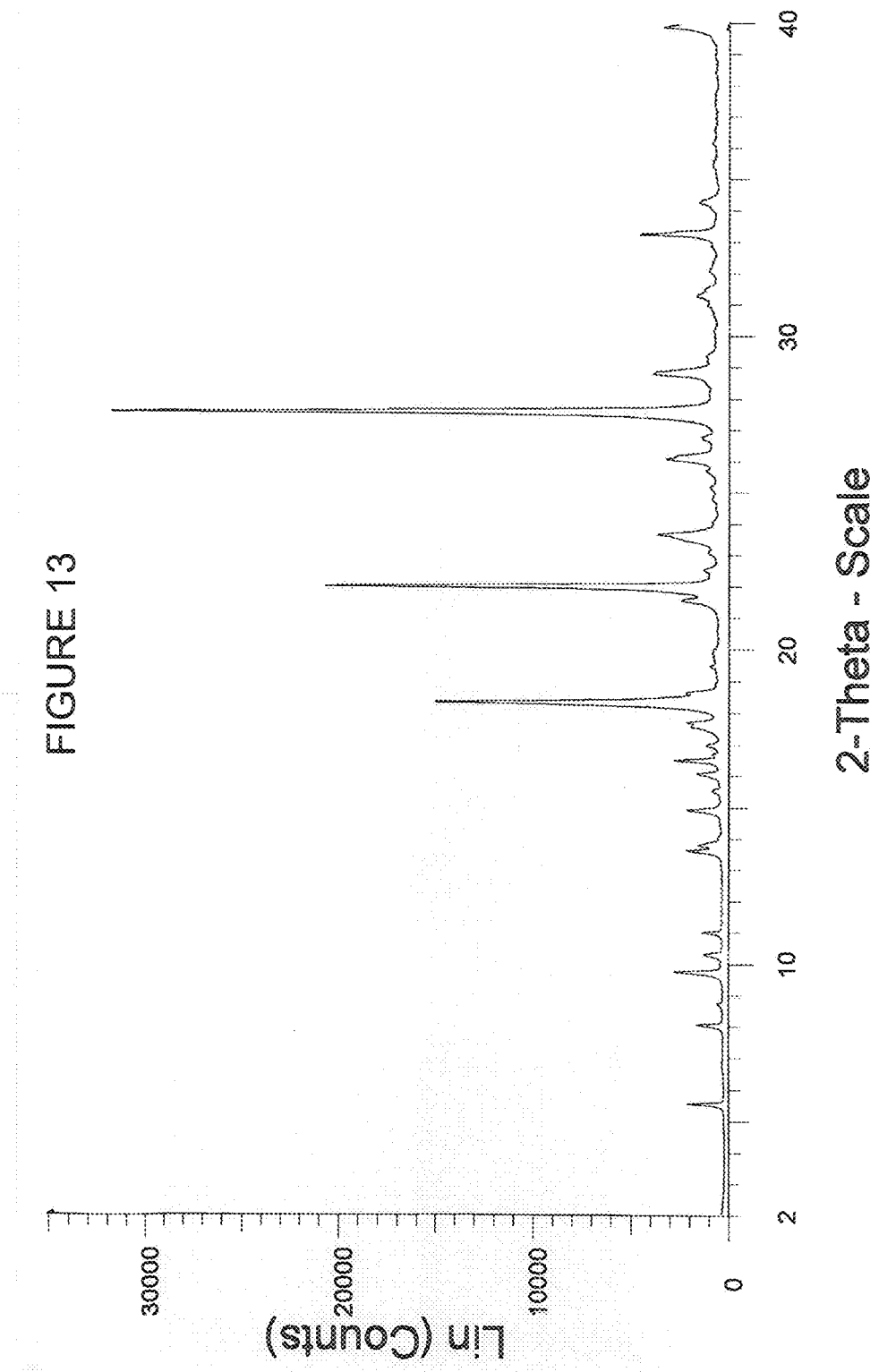

Provided herein is a mixed DMAC (dimethylacetamide)/toluene solvate of compound (I). FIGS. 11-13 show DSC, TGA, and XRPD spectra for the mixed DMAC/toluene solvate of compound (I), respectively. The mass loss between 90 and 130° C. of the TGA shows that this solvate contains 2 moles of DMAC for one mole of compound (I) and also contains one mole of toluene. The mass loss of 31.6% also corresponds to a structure containing two mole of DMAC and one mole of toluene. Accordingly, there exists a mixed DMAC/toluene solvate of compound (I). This is also supported by NMR (not shown).

In some embodiments, the mixed DMAC/toluene solvate of compound (I) is identifiable on the basis of characteristic peaks in an X-ray powder diffraction analysis. In one embodiment, the mixed DMAC/toluene solvate of compound (I) exhibits an X-ray powder diffraction pattern having characteristic peaks expressed in degrees 2-Theta at angles of 18.3°±0.3°, 22.0°±0.3° and 27.6°±0.3°. In another embodiment, the DMAC solvate of compound (I) exhibits an X-ray powder diffraction pattern substantially in accordance with FIG. 13 or Table 3, or both FIG. 13 and Table 3.

In some embodiments, the mixed DMAC/toluene solvate of compound (I) is identifiable on the basis of a characteristic peak observed in a differential scanning calorimetry thermogram. In one embodiment, the DMAC solvate of compound (I) exhibits a differential scanning calorimetry thermogram having a characteristic peak expressed in units of ° C. at a temperature of about 163±2° C. (e.g., 163.5±2° C. In another embodiment, the DMAC solvate of compound (I) exhibits a differential scanning calorimetry thermogram substantially in accordance with FIG. 11.

In other embodiments, the mixed DMAC/toluene solvate of compound (I) is identifiable on the basis of a characteristic thermogravimetry curve. In one embodiment, the DMAC solvate of compound (I) exhibits a thermogravimetry curve substantially in accordance with FIG. 12.

Figure 14:
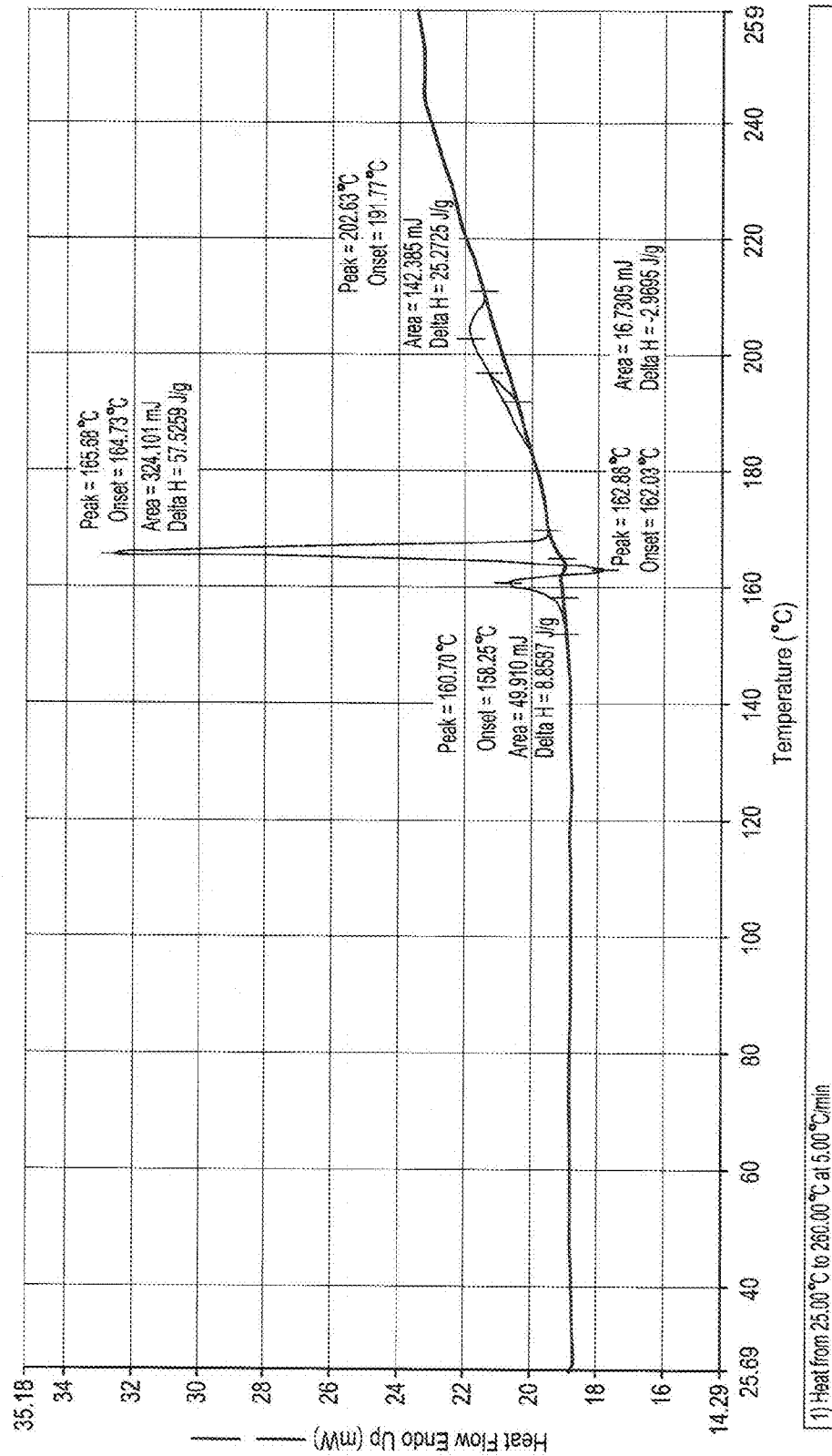
FIGS. 14-16 show DSC, TGA, and XRPD spectra for the DMSO-solvate of compound (I) provided herein.
Figure 15:
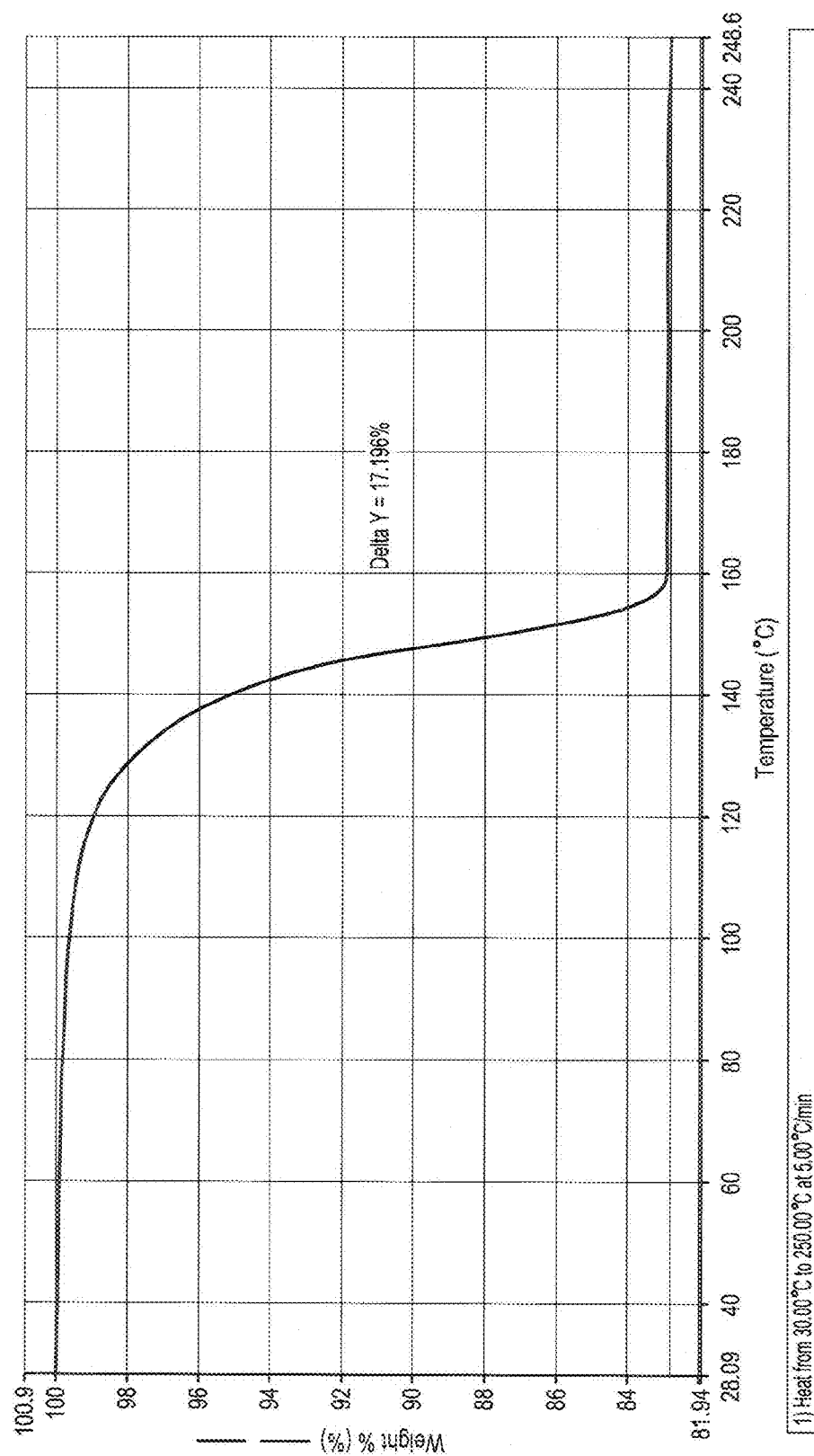
Figure 16:
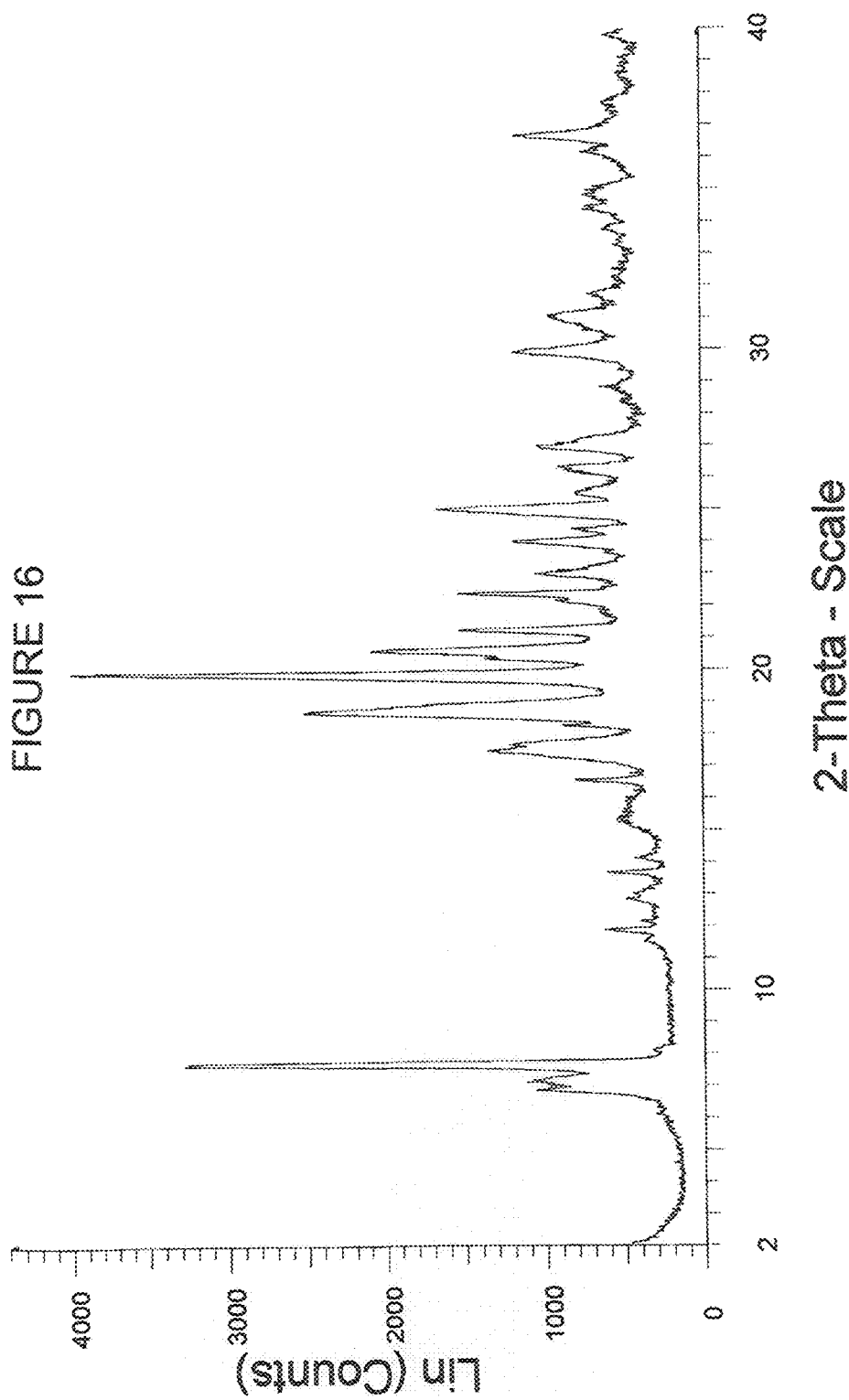

FIGS. 14-16 show DSC, TGA, and XRPD spectra for the DMSO solvate of compound (I), respectively. Analysis by NMR (not shown) shows that there is one mole of DMSO for one molecule of compound (I). The mass loss of 17.2% is consistent with this analysis.

In some embodiments, the DMSO solvate of compound (I) is identifiable on the basis of characteristic peaks in an X-ray powder diffraction analysis. In one embodiment, the DMSO solvate of compound (I) exhibits an X-ray powder diffraction pattern having characteristic peaks expressed in degrees 2-Theta at angles of 7.6°±0.3°, 18.6°±0.3° and 19.8°±0.3°. In another embodiment, the mixed DMAC/toluene solvate of compound (I) exhibits an X-ray powder diffraction pattern substantially in accordance with FIG. 16 or Table 4, or both FIG. 16 and Table 4.

In some embodiments, the DMSO solvate of compound (I) is identifiable on the basis of a characteristic peak observed in a differential scanning calorimetry thermogram. In one embodiment, the DMSO solvate of compound (I) exhibits a differential scanning calorimetry thermogram having a characteristic peak expressed in units of ° C. at a temperature of about 165±2° C. (e.g., 165.7±2° C. In another embodiment, the DMSO solvate of compound (I) exhibits a differential scanning calorimetry thermogram substantially in accordance with FIG. 14.

In other embodiments, the DMSO solvate of compound (I) is identifiable on the basis of a characteristic thermogravimetry curve. In one embodiment, the DMSO solvate of compound (I) exhibits a thermogravimetry curve substantially in accordance with FIG. 15.

DSC analyses for the mixed DMAC/toluene solvate and DMSO solvate were performed with a Perkin Elmer DSC Diamond. The software used to analyze the raw data is Pyris (Perkin Elmer). The temperature rate is 5° C./min. The TGA analyses were performed with a Perkin Elmer Pyris 1 TGA. The software used to analyze the raw data is Pyris (Perkin Elmer). The temperature rate is 5° C./min.

Pharmaceutical Compositions

In one aspect, pharmaceutical compositions are provided comprising N-(3-{[(2Z)-3-[(2-chloro-5-methoxyphenyl) amino]quinoxalin-2(1H)-ylidene]sulfamoyl}phenyl)-2-methylalaninamide or a pharmaceutically acceptable salt or solvate thereof. Such pharmaceutical compositions can comprise a pharmaceutically acceptable carrier or diluent. In some embodiments, the active ingredient of the pharmaceutical composition consists only of N-(3-{[(2Z)-3-[(2-chloro-5-methoxyphenyl)amino]quinoxalin-2(1H)-ylidene] sulfamoyl}phenyl)-2-methylalaninamide or a pharmaceutically acceptable salt or solvate thereof, in the absence of other tautomeric forms. In some embodiments, the active ingredient of the pharmaceutical compositions contains greater than 90%, greater than 95%, greater than 96%, greater than 97%, greater than 98%, greater than 99% or greater than 99.9% N-(3-{[(2Z)-3-[(2-chloro-5-methoxyphenyl)amino]quinoxalin-2(1H)-ylidene]sulfamoyl}phenyl)-2-methylalaninamide, or pharmaceutically acceptable salt or solvate thereof.

In other aspects, pharmaceutical compositions are provided comprising compound (I), for example polymorph A, pseudo-polymorph B, or polymorph E of compound (I), and a pharmaceutically acceptable carrier or diluent. For example, a pharmaceutical composition is provided comprising polymorph E, and a pharmaceutically acceptable carrier or diluent.

The term "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1% to 99.9% (more preferably, 0.5 to 90%) of active ingredient in combination with a pharmaceutically acceptable carrier.

The polymorphs described herein can be combined with a pharmaceutically acceptable carrier according to conventional pharmaceutical compounding techniques. As used herein, "pharmaceutically acceptable carrier" may include any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compound (I) such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Furthermore, the carrier may take a wide variety of forms depending on the form of the preparation desired for administration, e.g. oral, nasal, rectal, vaginal, parenteral (including intravenous injections or infusions). In preparing compositions for oral dosage form any of the usual pharmaceutical media may be employed. Usual pharmaceutical media include, for example, water, glycols, oils, alcohols, flavoring agents, preservatives, coloring agents, and the like in the case of oral liquid preparations (such as for example, suspensions, solutions, emulsions and elixirs); aerosols; or carriers such as starches, sugars, microcrystalline cellulose, diluents, granulating agents, lubricants, binders, disintegrating agents and the like, in the case of oral solid preparations (such as for example, powders, capsules, and tablets).

Wetting agents, emulsifiers and lubricants, such as sodium lauryl sulfate and magnesium stearate, as well as coloring agents, release agents, coating agents, sweetening, flavoring and perfuming agents, preservatives and antioxidants also can be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, tocopherols, and the like; and metal chelating agents, such as citric acid, ethylenediamine tetraacetic acid (EDTA), sorbitol, tartaric acid, phosphoric acid, and the like.

Pharmaceutical compositions comprising compound (I) may be formulated to have any concentration desired. In some embodiments, the composition is formulated such that it comprises at least a therapeutically effective amount. In some embodiments, the composition is formulated such that it comprises an amount that would not cause one or more unwanted side effects.

Because of their ease of administration, tablets and capsules may represent the most advantageous oral dosage unit form, in which case solid pharmaceutical carriers may be employed. If desired, tablets may be coated by techniques known to those in the art.

In one embodiment, the pharmaceutical composition comprises a polymorph of N-(3-{[(2Z)-3-[(2-chloro-5-methoxyphenyl)amino]quinoxalin-2(1H)-ylidene]sulfamoyl}phenyl)-2-methylalaninamide in a crystalline, solvate, hydrate or amorphous form other than polymorph E. In another embodiment, the pharmaceutical composition further comprises polymorph A of compound (I). Polymorph A of compound (I) is also referred to herein as "polymorph A". In yet another embodiment, the pharmaceutical composition further comprises pseudo-polymorph B of compound (I). Pseudo-polymorph B of compound (I) is a sesquihydrate form of compound (I).

In certain embodiments, the pharmaceutical composition comprises varying amounts of polymorph E, based on the total weight of N-(3-{[(2Z)-3-[(2-chloro-5-methoxyphenyl)amino]quinoxalin-2(1H)-ylidene]sulfamoyl}phenyl)-2-methylalaninamide in the composition. In one embodiment, the pharmaceutical composition comprises less than 0.1% by weight of polymorph E. In another embodiment, the pharmaceutical composition comprises less than 1% by weight of polymorph E. In another embodiment, the pharmaceutical composition comprises less than 10% by weight of polymorph E. In another embodiment, the pharmaceutical composition comprises less than 25% by weight of polymorph E. In another embodiment, the pharmaceutical composition comprises less than 50% by weight of polymorph E. In another embodiment, the pharmaceutical composition comprises less than 99% by weight of polymorph E.

Pharmaceutical compositions include those suitable for oral, sublingual, nasal rectal, vaginal, topical, buccal and parenteral (including subcutaneous, intramuscular, and intravenous) administration, although the most suitable route will depend on the nature and severity of the condition being treated. The compositions may be conveniently presented in unit dosage form, and prepared by any of the methods well known in the art of pharmacy. In certain embodiments, the pharmaceutical composition is formulated for oral administration in the form of a pill, capsule, lozenge or tablet. In other embodiments, the pharmaceutical composition is in the form of a suspension.

Polymorph E is suitable as an active agent in pharmaceutical compositions that are efficacious particularly for treating protein kinase-associated disorders, especially PI3K-associated disorders, e.g., cancer. The pharmaceutical composition in various embodiments has a pharmaceutically effective amount of polymorph E, along with other pharmaceutically acceptable excipients, carriers, fillers, diluents and the like.

The terms "effective amount" or "pharmaceutically effective amount" or "therapeutically effective amount" refer to a sufficient amount of an agent to provide the desired biological, therapeutic, and/or prophylactic result. That result can be reduction, amelioration, palliation, lessening, delaying, and/or alleviation of one or more of the signs, symptoms, or causes of a disease, or any other desired alteration of a biological system. In reference to cancer, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay recurrence. An effective amount can be administered in one or more administrations. The effective amount of the drug or composition may: (i) reduce the number of cancer cells; (ii) reduce tumor size; (iii) inhibit, retard, slow to some extent, and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer. The amount can vary depending on such factors as the size and weight of the subject, the type of illness, or the particular compound of the invention. The amount also can vary depending on the compound, the disease state and its severity, the age of the patient to be treated, and the like. The effective amount can be determined by one of ordinary skill in the art having regard to their knowledge and to this disclosure.

The regimen of administration can affect what constitutes a pharmaceutically effective amount. Polymorph E, and compositions comprising polymorph E, can be administered to the subject either prior to or after the onset of a PI3K-associated disorder. Further, several divided dosages, as well as staggered dosages can be administered daily or sequentially, or the dose can be continuously infused, or can be a bolus injection. Further, the dosages can be proportionally increased or decreased as indicated by the exigencies of the therapeutic or prophylactic situation.

Process

In another aspect, provided herein is a process for the preparation of polymorph E, which comprises the following steps: (a) dissolving N-(3-{[(2Z)-3-[(2-chloro-5-methoxyphenyl)amino]quinoxalin-2(1H)-ylidene]sulfamoyl}phenyl)-2-methylalaninamide in a first solvent, (b) optionally adding a second solvent, and (e) optionally seeding the mixture, such that said polymorph is formed.

In one embodiment, the process comprises the following steps: (a) dissolving compound (I) in THF, (b) concentrating the mixture, (c) reducing the temperature of the mixture, (d) adding ethanol to the mixture, (e) seeding the mixture, and (f) lowering the temperature of the mixture, such that polymorph E is formed.

In another embodiment, the process comprises the following steps: (a) dissolving compound (I) in dimethylacetamide, (b) adding toluene, (c) lowering the temperature of the mixture, (d) filtering solids from the mixture and washing the solids, (e) suspending the filtered solids in ethanol, and (f) seeding the mixture, such that polymorph E is formed.

In yet another embodiment, the process comprises the following steps: (a) dissolving compound (I) in DMSO, (b) adding ethanol to the mixture, (c) filtering solids from the mixture, (d) suspending the solids in ethanol, and (e) seeding the mixture, such that polymorph E is formed.

In yet another embodiment, the process comprises the following steps: (a) dissolving compound (I) in DMAC, (b) adding ethanol to the mixture, (c) filtering solids from the mixture, (d) suspending the solids in ethanol, and (e) seeding the mixture, such that polymorph E is formed.

As used herein, the term "seed" can be used as a noun to describe one or more crystals of a crystalline compound (I) (e.g., polymorph E). The term "seed" can also be used as a verb to describe the act of introducing said one or more crystals of a crystalline compound (I) into an environment (including, but not limited to e.g., a solution, a mixture, a suspension, or a dispersion) thereby resulting in the formation of more crystals of the crystalline compound (I).

Methods and Uses

Compound (I) is useful for the treatment of conditions and disorders mediated by PI3K in a subject. Accordingly, methods are provided for treating a condition or disorder mediated by PI3K in a subject, e.g., a patient, comprising administering to the subject a therapeutically effective amount of compound (I) (e.g., polymorph E).

"Conditions mediated by PI3K" or "disorders mediated by PI3K" refer to pathologic conditions that depend on the activity of one or more PI3K kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like). In one example, the condition is cancer.

"Administration" and variants thereof (e.g., "administering" a compound) in reference to the compound of the invention means introducing the compound or a prodrug of the compound into the system of the animal in need of treatment. When the compound of the invention or prodrug thereof is provided in combination with one or more other active agents (e.g., surgery, radiation, and chemotherapy, etc.), "administration" and its variants are each understood to include concurrent and sequential introduction of the compound or prodrug thereof and other agents.

The term "subject" is intended to include organisms, e.g., prokaryotes and eukaryotes, that are capable of suffering from or afflicted with a disease, disorder or condition associated with the activity of a protein kinase like PI3Kα. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancer. In another embodiment, the subject is a cell.

"Patient" for the purposes of the present invention includes humans and other animals, particularly mammals, and other organisms. Thus the methods are applicable to both human therapy and veterinary applications. In a specific embodiment the patient is a mammal, and in a more specific embodiment the patient is human.

"Treating" or "treatment" of a disease, disorder, or syndrome, as used herein, includes (i) preventing the disease, disorder, or syndrome from occurring in a human, i.e., causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

In another embodiment, provided herein is a method of treating cancer in a subject comprising administering to the subject a therapeutically effective amount of compound (I) (e.g., polymorph E).

In another aspect, provided herein is a method for the treatment of disorders mediated by PI3K, comprising administering to a patient in need of such treatment an effective amount of polymorph E or a pharmaceutical composition comprising polymorph E. In one embodiment, the disorder is a cellular proliferative disease. In one example, the cellular proliferative disease is cancer.

In some aspects, a disorder mediated by PI3K includes disorders and states (e.g., a disease state) which are associated with abnormal cell growth, abnormal cell proliferation, or aberrant activity of PI3K. Examples of Pin1-associated states include cancer, undesirable cell growth, and/or tumor growth.

"Cancer" includes, but is not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

In some embodiments, the disorder is selected from breast cancer, colorectal cancer, endometrial cancer, gastric carcinoma, glioblastoma, hepatocellular carcinoma, small cell lung cancer, non-small cell lung cancer, melanoma, ovarian cancer, pancreatic cancer, prostate carcinoma, and thyroid carcinoma.

In other embodiments, methods are provided for treating disorders selected from breast cancer, colorectal cancer, endometrial cancer, gastric carcinoma, glioblastoma, hepatocellular carcinoma, small cell lung cancer, non-small cell lung cancer, melanoma, ovarian cancer, pancreatic cancer, prostate carcinoma, and thyroid carcinoma, comprising administering to a patient in need of such treatment an effective amount of compound (I) or a pharmaceutical composition comprising compound (I).

In other embodiments, provided herein is a method for the treatment of disorders selected from solid tumors, non-small cell lung cancer, colon cancer, breast cancer, endometrial cancer, prostate cancer and sarcoma comprising administering to a patient in need of such treatment an effective amount of compound (I), or a pharmaceutical composition comprising compound (I).

In a particular embodiment, provided herein is a method for the treatment of metastatic breast cancer, comprising administering to a patient in need of such treatment an effective amount of compound (I), or a pharmaceutical composition comprising compound (I).

In another particular embodiment, provided herein is a method for the treatment of lymphoma, comprising administering to a patient in need of such treatment an effective amount of compound (I), or a pharmaceutical composition comprising compound (I).

In still another particular embodiment, provided herein is a method for the treatment of glioblastoma, comprising administering to a patient in need of such treatment an effective amount of compound (I), or a pharmaceutical composition comprising compound (I).

In another aspect, provided herein is the use of compound (I) for the preparation of a medicament for the treatment of disorders mediated by PI3K. In one embodiment, the disorder is a cellular proliferative disease. In another embodiment, the cellular proliferative disease is cancer. In certain embodiments, the cancer is selected from the list above. In other embodiments, the disorder is selected from breast cancer, colorectal cancer, endometrial cancer, gastric carcinoma, glioblastoma, hepatocellular carcinoma, small cell lung cancer, non-small cell lung cancer, melanoma, ovarian cancer, pancreatic cancer, prostate carcinoma, and thyroid carcinoma.

Another specific embodiment of the invention is a method of inhibiting PI3K in a cell, comprising contacting a cell in which inhibition of PI3K is desired with Compound (I).

Another specific embodiment of the invention is a method of treating a disease, disorder, or syndrome mediated by PI3K which method comprises administering to a patient a pharmaceutical composition comprising a therapeutically effective amount of Compound (I).

More specifically, the disease is cancer. Even more specifically, the cancer is breast cancer, colon cancer, rectal cancer, endometrial cancer, gastric carcinoma, glioblastoma, hepatocellular carcinoma, small cell lung cancer, non-small cell lung cancer, melanoma, ovarian cancer, cervical cancer, pancreatic cancer, prostate carcinoma, acute myelogenous leukemia (AML), chronic myelogenous leukemia (CIVIL), or thyroid carcinoma. Even more specifically, the cancer is ovarian cancer, cervical cancer, breast cancer, colon cancer, rectal cancer, or glioblastoma.

Accordingly, in one embodiment, provided herein is a method of treating endometrial cancer comprising administering to a subject in need thereof a therapeutically effective amount of Compound (I).

In another embodiment, provided herein is a method of treating ovarian cancer comprising administering to a subject in need thereof a therapeutically effective amount of Compound (I).

In another embodiment, provided herein is a method of treating non-small cell lung cancer (NSCLC) comprising administering to a subject in need thereof a therapeutically effective amount of Compound (I).

In another embodiment, provided herein is a method of treating breast cancer comprising administering to a subject in need thereof a therapeutically effective amount of Compound (I).

In another embodiment, provided herein is a method of treating a lymphoma comprising administering to a subject in need thereof a therapeutically effective amount of Compound (I).

In another embodiment, provided herein is a method of treating a solid tumor comprising administering to a subject in need thereof a therapeutically effective amount of Compound (I).

In another embodiment, provided herein is a method of treating glioblastoma comprising administering to a subject in need thereof a therapeutically effective amount of Compound (I).

In other embodiments, provided herein is a method for the treatment of disorders selected from breast cancer, colorectal cancer, endometrial cancer, gastric carcinoma, glioblastoma, hepatocellular carcinoma, small cell lung cancer, non-small cell lung cancer, melanoma, ovarian cancer, pancreatic cancer, prostate carcinoma, and thyroid carcinoma, comprising administering to a patient in need of such treatment an effective amount of polymorph E or a pharmaceutical composition comprising polymorph E.

In other embodiments, provided herein is a method for the treatment of disorders selected from solid tumors, non-small cell lung cancer, colon cancer, breast cancer, endometrial cancer, prostate cancer and sarcoma comprising administering to a patient in need of such treatment an effective amount of polymorph E, or a pharmaceutical composition comprising polymorph E.

In a particular embodiment, provided herein is a method for the treatment of metastatic breast cancer, comprising administering to a patient in need of such treatment an effective amount of polymorph E, or a pharmaceutical composition comprising polymorph E.

In another particular embodiment, provided herein is a method for the treatment of lymphoma, comprising administering to a patient in need of such treatment an effective amount of polymorph E, or a pharmaceutical composition comprising polymorph E.

In still another particular embodiment, provided herein is a method for the treatment of glioblastoma, comprising administering to a patient in need of such treatment an effective amount of polymorph E, or a pharmaceutical composition comprising polymorph E.

In another aspect, provided herein is the use of polymorph E for the preparation of a medicament for the treatment of disorders mediated by PI3K. In one embodiment, the disorder is a cellular proliferative disease. In one example, the cellular proliferative disease is cancer. In certain embodiments, the cancer is selected from the list above. In other embodiments, the disorder is selected from breast cancer, colorectal cancer, endometrial cancer, gastric carcinoma, glioblastoma, hepatocellular carcinoma, small cell lung cancer, non-small cell lung cancer, melanoma, ovarian cancer, pancreatic cancer, prostate carcinoma, and thyroid carcinoma.

Another specific embodiment of the invention is a method of inhibiting PI3K in a cell, comprising contacting a cell in which inhibition of PI3K is desired with polymorph E.

Another specific embodiment of the invention is a method of treating a disease, disorder, or syndrome mediated by PI3K which method comprises administering to a patient a pharmaceutical composition comprising a therapeutically effective amount of polymorph E.

More specifically, the disease is cancer. Even more specifically, the cancer is breast cancer, colon cancer, rectal cancer, endometrial cancer, gastric carcinoma, glioblastoma, hepatocellular carcinoma, small cell lung cancer, non-small cell lung cancer, melanoma, ovarian cancer, cervical cancer, pancreatic cancer, prostate carcinoma, acute myelogenous leukemia (AML), chronic myelogenous leukemia (CIVIL), or thyroid carcinoma. Even more specifically, the cancer is ovarian cancer, cervical cancer, breast cancer, colon cancer, rectal cancer, or glioblastoma.

Accordingly, in one embodiment, provided herein is a method of treating endometrial cancer comprising administering to a subject in need thereof a therapeutically effective amount of polymorph E.

In another embodiment, provided herein is a method of treating ovarian cancer comprising administering to a subject in need thereof a therapeutically effective amount of polymorph E.

In another embodiment, provided herein is a method of treating non-small cell lung cancer (NSCLC) comprising administering to a subject in need thereof a therapeutically effective amount of polymorph E.

In another embodiment, provided herein is a method of treating breast cancer comprising administering to a subject in need thereof a therapeutically effective amount of polymorph E.

In another embodiment, provided herein is a method of treating a lymphoma comprising administering to a subject in need thereof a therapeutically effective amount of polymorph E.

In another embodiment, provided herein is a method of treating a solid tumor comprising administering to a subject in need thereof a therapeutically effective amount of polymorph E.

In another embodiment, provided herein is a method of treating endometrial cancer comprising administering to a subject in need thereof a therapeutically effective amount of polymorph E.

Another aspect of the invention is directed to employing Compound (I) (e.g., polymorph E) in a method of screening for candidate agents that bind to, for example PI3K. In that method, the protein is bound to a support, and a compound of the invention is added to the assay. Alternatively, the compound of the invention is bound to the support and the protein is added. Classes of candidate agents among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate agent to, for example, PI3K may be done in a number of ways. In one example, the candidate agent (Compound (I) (e.g., polymorph E)) is labeled, for example, with a fluorescent or radioactive moiety and binding determined directly. For example, this may be done by attaching all or a portion of the PI3K protein to a solid support, adding a labeled agent (for example a compound of the invention in which at least one atom has been replaced by a detectable isotope), washing off excess reagent, and determining whether the amount of the label is that present on the solid support. Various blocking and washing steps may be utilized as is known in the art.

The term "labeled" as used herein is meant to include both direct and indirect labeling with a compound that provides a detectable signal, for example, radioisotope, fluorescent tag, enzyme, antibodies, particles such as magnetic particles, chemiluminescent tag, or specific binding molecules, and the like. Specific binding molecules include pairs, such as biotin and streptavidin, digoxin and antidigoxin, and the like. For the specific binding members, the complementary member would normally be labeled with a molecule which provides for detection, in accordance with known procedures, as outlined above. The label can directly or indirectly provide a detectable signal.

Compound (I) (e.g., polymorph E) may also be used as competitors to screen for additional drug candidates. The terms "candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Compound (I) (e.g., polymorph E) is also useful in combination with known anti-cancer agents. Such known anti-cancer agents include the following: carboplatin, paclitaxel, erlotinib, and trastuzumab.

EXAMPLES

Example 1

Synthesis of Compound (I)

Figure 10:
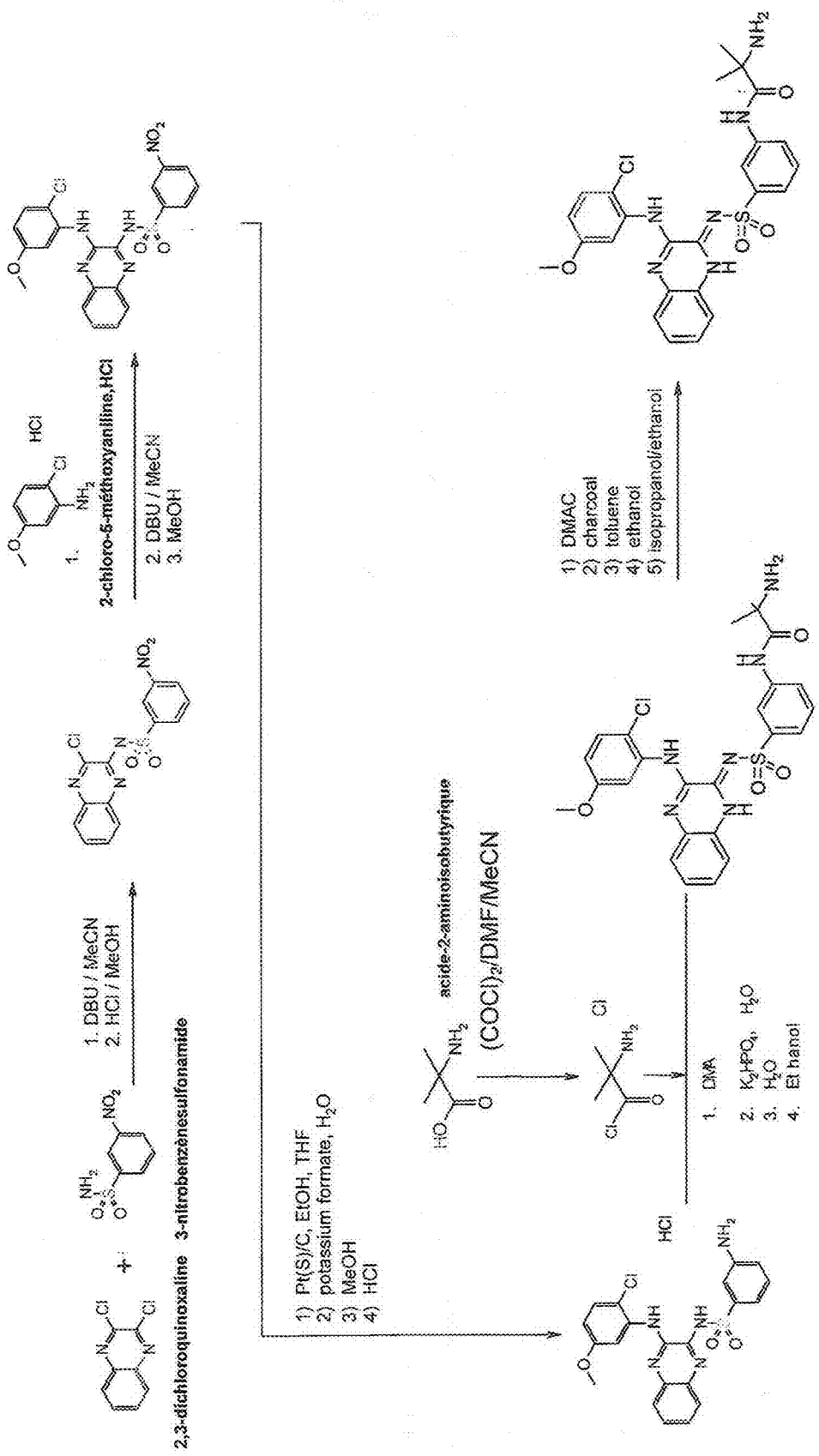
FIG. 10 depicts a synthesis scheme for preparing raw compound (I).

FIG. 10 depicts a synthesis scheme for preparing compound (I). A description of the scheme is provided below.

Synthesis of (N-(3-chloroquinoxalin-2-yl)-3-nitrobenzenesulfonamide)

1 kg of 2,3 dichloroquinoxaline and 1 kg of 3-nitrobenzenesulfonamide are mixed in 5 volumes of acetonitrile. The reaction mixture is heated to reflux. 2.3 kg of DBU and 1 volume of acetonitrile are added. After completion of the reaction, cool down at 5° C. Add 12 volumes of methanol and 1.53 kg of HCl, filter the reaction mixture. Wash the cake with 6 volumes of methanol and dry under vacuum.

Synthesis of (N-(3-((2-chloro-5-methoxyphenyl)amino)quinoxalin-2-yl)-3-nitrobenzenesulfonamide)

Prepare a solution with 0.585 kg of 2-chloro-5-methoxyaniline-HCl, 3.5 volumes of acetonitrile and 0.46 kg of DBU. (solution A) Mix 1 kg of N-(3-chloroquinoxalin-2-yl)-3-nitrobenzenesulfonamide and 5.5 volumes of acetonitrile. Heat to reflux. Add solution A and 1 volume of acetonitrile onto the reaction mixture. After completion of the reaction at reflux, cool down at 20° C., dilute with 10 volumes of methanol and filter. Wash the cake 3 times with 5 volumes of methanol and dry it under vacuum.

Synthesis of 3-amino-N-{3-[(2-chloro-5-methoxyphenyl)amino]quinoxalin-2-yl}benzenesulfonamide hydrochloride To 1 kg of N-{3-[(2-chloro-5-methoxyphenyl)amino]quinoxalin-2-yl}-3-nitrobenzenesulfonamide, add a catalytic amount of platinum sulfide on carbon (Pt(S)C), 6 volumes of THF, 0.16 volume of water and 2 volumes of ethanol. The reaction mixture is stirred and heated to reflux. An aqueous potassium formate solution (1.4 volume of water+0.69 kg of potassium formate) is added. The reaction mixture is stirred at reflux until completion of the reaction and cooled down at 50° C. After the addition of 10 volumes of methanol and a one hour stirring, the catalyst is filtered off and washed with 3.4 volumes of methanol. The filtered solution is cooled down at 20° C. 0.62 kg of HCl are added. The reaction mixture is stirred at 20° C., cooled down at 5° C. and filtered. The cake is washed with methanol (6 volumes) and dried under vacuum.

Synthesis of N-[3-({3-[(2-chloro-5-methoxyphenyl)amino]quinoxalin-2-yl}sulfamoyl)phenyl]-2-methylalaninamide (crude)

Synthesis of 2-methylalanyl chloride hydrochloride. To 0.42 kg of 2-amino-2-methylpropanoic acid, add 3.7 volumes of acetonitrile, 0.04 volume of dimethylformamide and 0.62 kg of oxalyl chloride. The reaction mixture is stirred at 20° C. until completion of the reaction and filtered. The cake is washed twice with 1 volume of acetonitrile and dried under vacuum.

To 1 kg of 3-amino-N-{3-[(2-chloro-5-methoxyphenyl)amino]quinoxalin-2-yl}benzenesulfonamide hydrochloride, add 8 volumes of dimethylformamide and 0.385 kg of 2-methylalanyl chloride hydrochloride at 5° C. After completion of the reaction, heat at 50° C. and add a solution made of K2HPO4 (1.4 kg), water (16.5 volumes) and ethanol (7.1 volumes). Cool down the reaction mixture at 10° C., stir 2 hours at 10° C. anf filter. The cake is washed 3 times with 10 volumes of water and dried under vacuum. Resulting from this process is crude N-(3-{[(2Z)-3-[(2-chloro-5-methoxyphenyl)amino]quinoxalin-2(1H)-ylidene]sulfamoyl}phenyl)-2-methylalaninamide in the form of pseudo-polymorph B.

Crude N-(3-{[(2Z)-3-[(2-chloro-5-methoxyphenyl)amino]quinoxalin-2(1H)-ylidene]sulfamoyl}phenyl)-2-methylalaninamide was recrystallized from dimethylacetamide and toluene using charcoal, followed by reslurry in ethanol, and finally washings by isopropanol/ethanol mixture, resulting in the compound in pure form.

Surprisingly and unexpectedly, the solid state compound recovered from this process was entirely N-(3-{[(2Z)-3-[(2-chloro-5-methoxyphenyl)amino]quinoxalin-2(1H)-ylidene]sulfamoyl}phenyl)-2-methylalaninamide. That is, while a number of tautomeric forms of the compound may exist, the instant process yielded a solid compound of only N-(3-{[(2Z)-3-[(2-chloro-5-methoxyphenyl)amino]quinoxalin-2(1H)-ylidene]sulfamoyl}phenyl)-2-methylalaninamide and not a mixture of tautomers, as confirmed by ssNMR.

Example 2

Preparation of Polymorph A

To 1 kg of crude N-(3-{[(2Z)-3-[(2-chloro-5-methoxyphenyl)amino]quinoxalin-2(1H)-ylidene]sulfamoyl}phenyl)-2-methylalaninamide, add 20 volumes of THF, heat to reflux, add 20 volumes of ethanol, maintain at reflux 30 minutes, cool down to 5° C., filter the slurry and wash the cake with ethanol (2 volumes). Reslurry the wet cake in 11 volumes of ethanol at reflux for 3 hours. Cool down at 5° C., filter and wash with 2 volumes of ethanol dry under vacuum.

Example 3

Preparation of Polymorph E

The X-ray powder diffraction analyses described herein were performed using a Bruker X D8 advance diffractometer using Cu-Kα1 radiation. The samples were investigated in a flat preparation. The detector was Lynx Eye. Generator settings for the X-ray tube were 40 kV and 40 mA. The data was collected in the 2-Theta range from 2 to 40°. The position sensitive detector was moved over this 2-Theta range in steps of 0.02° and intensities were collected for 0.2 seconds at each position. The measured data was evaluated and plotted with the Software EVA v12.

FT-IR spectra were recorded with an FT-IR spectrometer (Bruker, Vertex 70). The data was collected between 4000 and 650 cm-1. 10 scans were accumulated. The resolution was 4 cm$^{-1}$. The spectra are evaluated and plotted by the software OPUS V 5.0.

Process I

On laboratory scale, the following crystallization took place in a double jacket reactor; the temperature in the reactor was checked and controlled via the temperature in the double jacket. The stirring apparatus is a glasslock type and the speed of stirring was fixed at 400 rpm.

Figure 6:
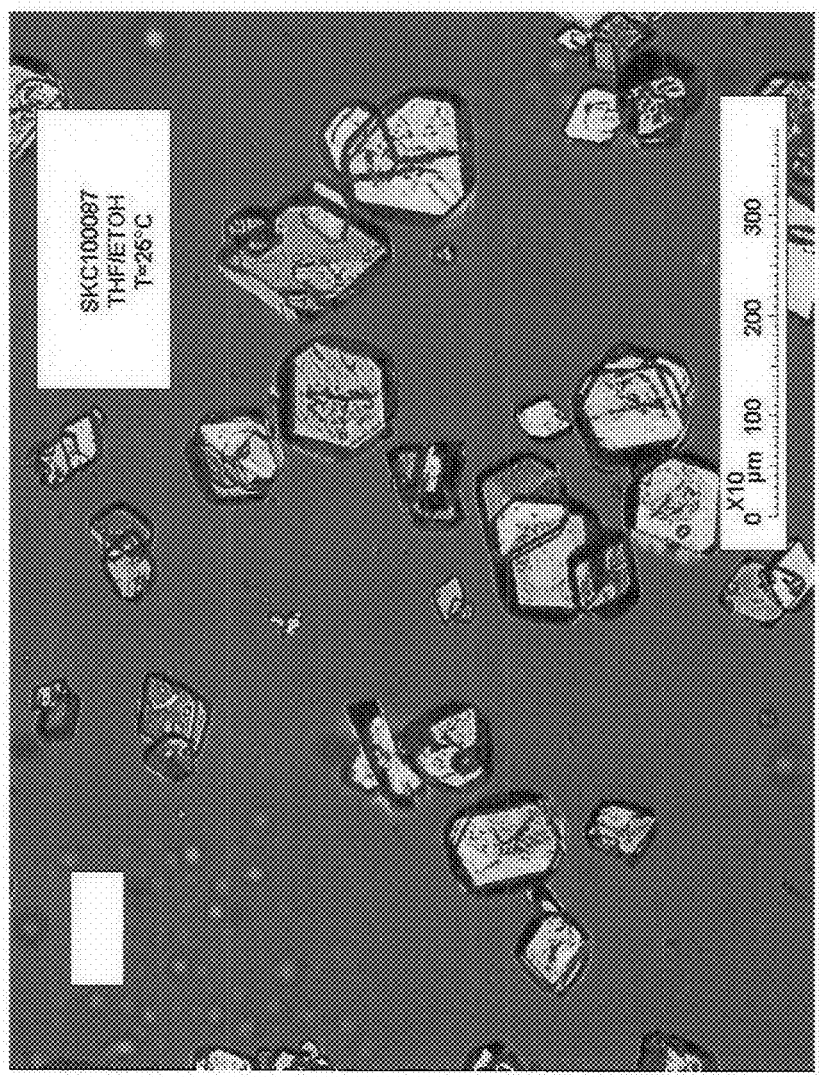
FIG. 6 depicts the results of optical microscopy of polymorph E.

5 g of raw compound (I) was combined with 50 V (250 mL) of THF and dissolved at the reflux. The total dissolution was observed at 45° C. The mixture was then concentrated via distillation to 20 residual volumes THF. At the end of distillation the temperature was lowered to 50° C., and the mixture was left in isotherm for 30 minutes. The crystallization began during this isotherm. 20 V of ethanol were quickly added at 50° C. 1% of seed (polymorph E) was put in suspension in 1 ml of ethanol and then introduced into the THF/ethanol solution. The solution was held at a temperature of 50° C. for one hour, then the temperature was lowered to 25° C. with a cooling rate of 20° C./hour. After roughly ten hours at 25° C., medium was filtered, then washed with two volumes of ethanol, then the wet product was dried in vacuum conditions at a temperature of 50° C. for 24 hours. The crystals so obtained were observed by optical microscopy. See FIG. 6.

Process II

On laboratory scale, the following crystallization took place in a double jacket reactor; the temperature in the reactor was checked and controlled via the temperature in the double jacket. The stirring apparatus is a glasslock type and the speed of stirring was fixed at 350 rpm.

Figure 7:
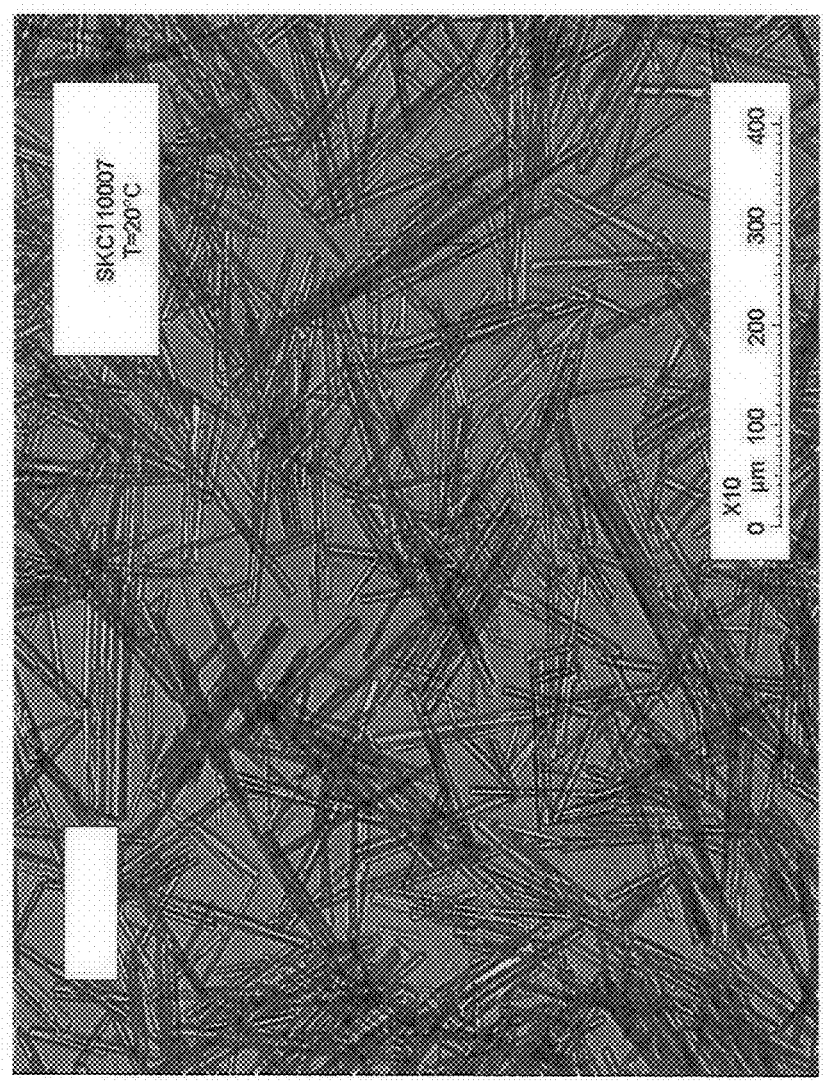
FIG. 7 depicts optical microscopy results of the mixed DMAC/toluene solvate form of compound (I).

10 g of raw compound (I) was combined with 10V (100 mL) of dimethylacetamide, the temperature of the double jacket was fixed at 95° C., and the compound was allowed to dissolve. The mixture was lowered to 70° C. and 5V (50 ml) of toluene were added. The crystallization began during this time. The mixture was then heated up to 90° C., maintained one hour at that temperature and lowered to 20° C. with a cooling rate of −10° C./hour. Before filtration, an aliquot of suspension was withdrawn and observed by optical microscopy. The crystals of solvate appear under the shape of fine rods. See FIG. 7. The suspension was filtered, then washed three times: twice with isopropanol (20 ml for each of the washes), then once with ethanol (10 ml), to yield the DMAC solvate of compound (I).

Figure 8:
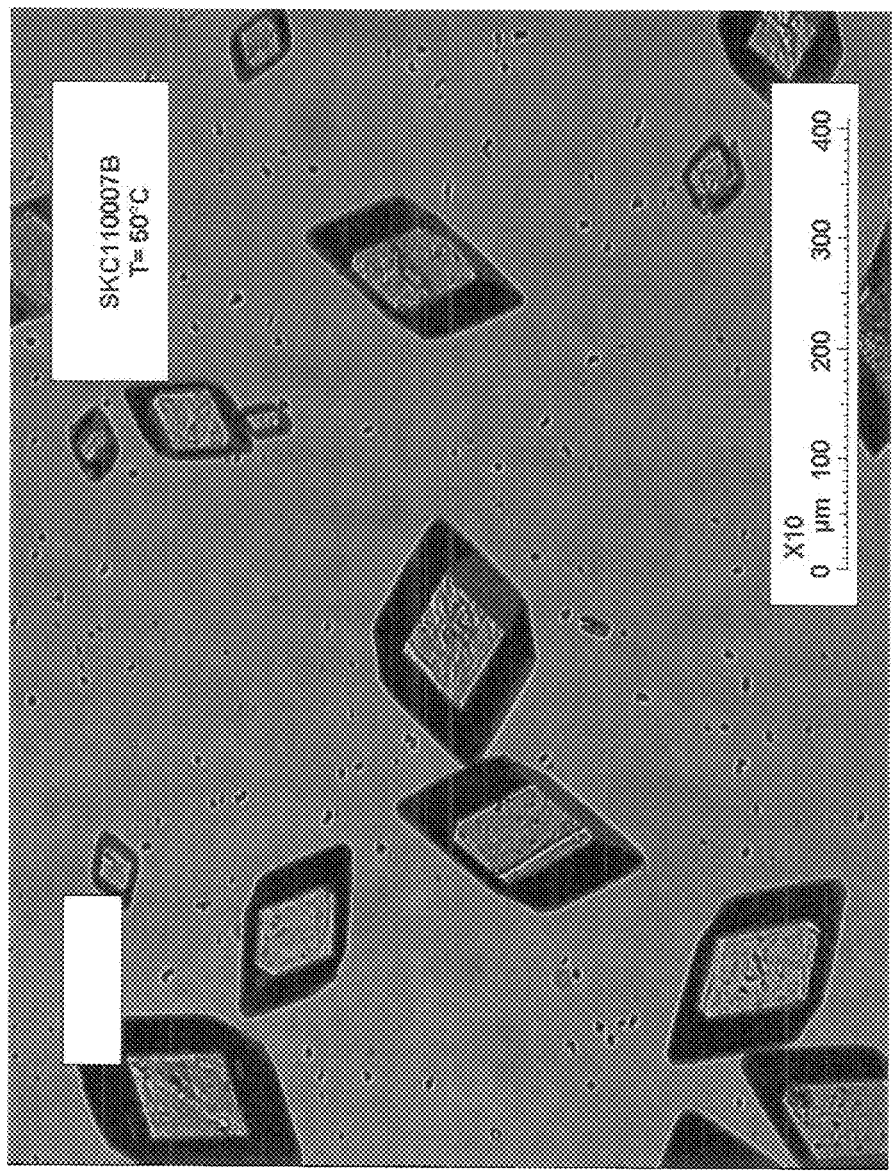
FIG. 8 depicts additional results of optical microscopy of polymorph E.
Figure 9:
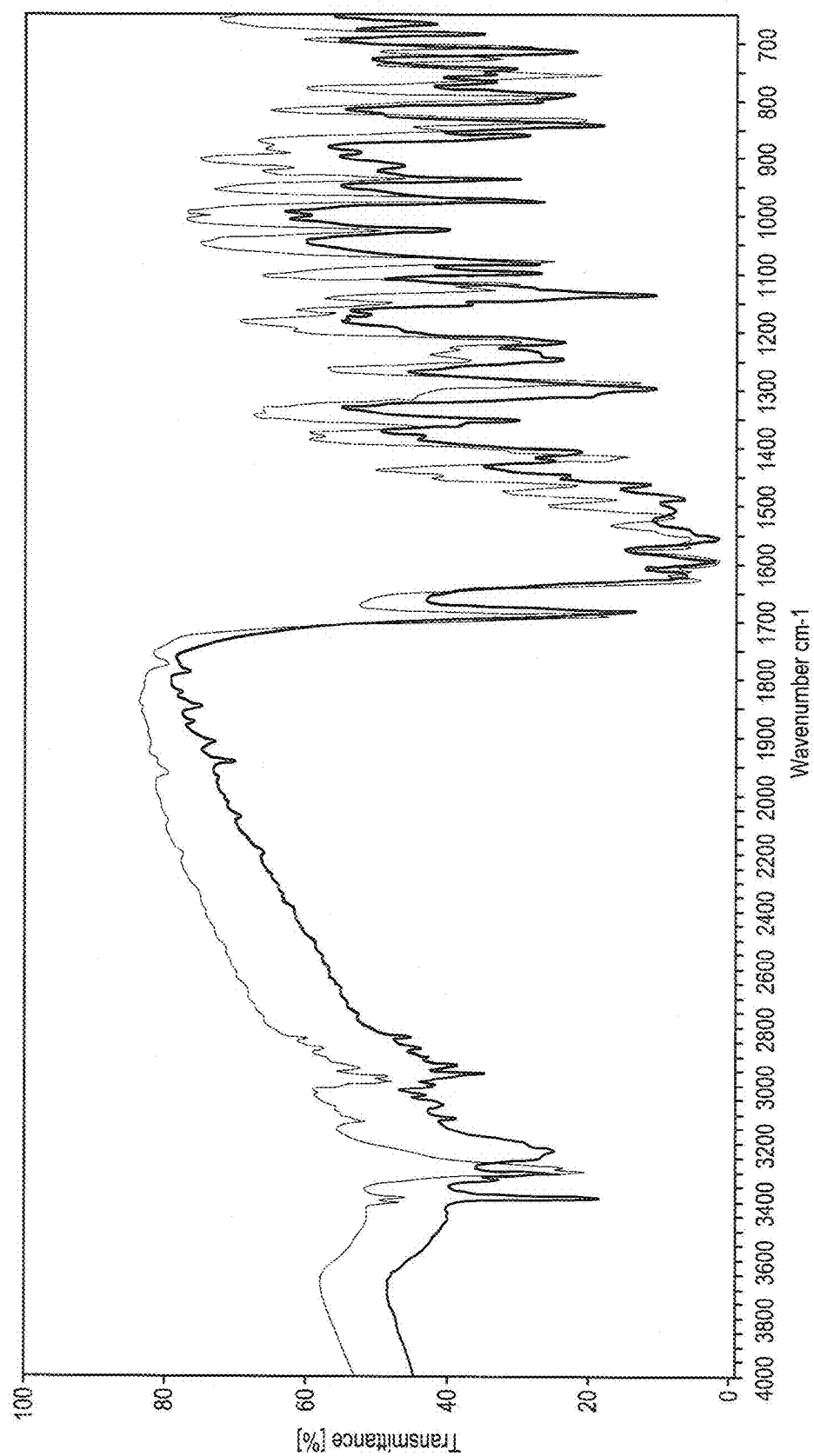
FIG. 9 depicts over-layed FT-IR spectra of raw compound (I) (upper spectrum) and polymorph E (lower spectrum).

The wet powder was re-slurried in 10 Volumes of ethanol at the temperature of 50° C., with a speed of stirring of 200 rpm, and then seeded with 1% (w/w) of polymorph E. The mixture is maintained in isotherm under stirring for several hours. The polymorphic conversion to polymorph E takes place during this stage. It is possible to accelerate this polymorphic transformation by increasing the temperature from 50° C. to 70° C. The temperature was lowered again to 50° C. for filtration. This transformation can be followed by optical microscopy, by Raman spectroscopy and Lasentec probe. The crystals of polymorph E appear in the shape of rhombohedric particles. See FIG. 8.

When the transformation was complete, the mixture was filtered at 50° C., then crystals were washed once with isopropanol (20 ml) and again with a volume of ethanol (10 ml). Crystals were dried in statics (vacuum tray dryer or oven ventilated tray dryer at the respective temperatures of 70° C. and 110° C.) for 12 at least hours.

The yield of this process was 84%. The obtained crystals were analyzed by X-ray diffraction to confirm that polymorph E was obtained, then analyzed for purity by HPLC. For this trial, the purity was measured at 99.7%.

The content of residual solvents also was measured and found to be: dimethylacetamide (256 ppm); isopropanol (106 ppm); tetrahydrofuran (<38 ppm); ethanol (1667 ppm).

Process III

On laboratory scale, the following crystallization took place in a double jacket reactor; the temperature in the reactor was checked and controlled via the temperature in the double jacket. The stirring apparatus is a glasslock type and the speed of stirring was fixed at 350 rpm.

10 g of raw compound (I) was suspended in 5V (50 mL) of DMSO, and then dissolved at a temperature of 90° C., the temperature of the mixture being controlled via the double jacket. The mixture then was cooled down to 70° C. with a cooling rate of −20° C./h. After an isotherm at 70° C. of several hours, 5V of ethanol was added. Then, the mixture was cooled down to the temperature of 20° C. with a rate of −20° C./h. The obtained suspension was filtered on a filter plan (diameter=6 cm; porosity=10 μm). The cake was washed twice with 2V of isopropanol and 1V of ethanol. The obtained solid was white.

The wet product was re-slurried in 10V of ethanol at the temperature of 70° C. at a stirring rate of 200 rpm. The mixture was seeded with 0.5 to 1% w/w of polymorph E. The polymorphic transformation occurred with a medium color change from white to fluorescent yellow characteristic of polymorph E. The mixture was left in isotherm at 70° C. for two hours, then cooled down to 50° C. and filtered. The mixture was washed twice with isopropanol (2 volumes for every wash), then a new wash with ethanol was performed (1V). The solid was dried in a vacuum tray dryer at 70° C. for 12 to 24 hours. The yield was about 84%. The purity of the solid was 99.8% (as measured by HPLC). The crystals were analyzed by X-ray diffraction and confirmed to be polymorph E. The residual solvent was measured by headspace analysis and was found to be: dimethylsulfoxide (59-82 ppm); isopropanol (4-89 ppm); ethanol (1337-1865 ppm).

Process IV

Compound (I) (polymorph A) was suspended in THF/Ethanol 77/23% (v/v) with magnetic stirring at room temperature (23° C.). After 24 hours, the suspension was filtered, the solid was dried and analyzed by X-ray powder diffraction. The solid was determined to be polymorph E.

Example 4

Characterization of Polymorph E

Polymorph E was characterized using optical microscopy, X-Ray powder diffraction, differential scanning calorimetry, thermogravimetric analysis and Infrared spectroscopy (FT-IR).

By optical microscopy, polymorph E appeared as large and thick plates. See FIG. 6.

By FT-IR spectroscopy, using a Brucker Vertex 70 infrared spectrometer, considerable differences were noted between the starting material form of raw compound (I) and polymorph E in spectral region between 3000 and 3400 cm-1.

Differential scanning calorimetry (DSC) analysis showed that polymorph E presents a melting point of 231° C.-233° C. with an associated enthalpy of fusion of about 114 J/g (e.g., 114 J/g±10 J/g). These values, following the rules of Burger, indicate a monotropic relationship between polymorphs A and E, with polymorph E being the more stable one.

A solid mixture of polymorphs A and E was analyzed by DSC. It was observed on the pattern an endotherm at 115° C. followed by an exothermic beginning at 219° C. This corresponds to the fusion of polymorph A followed by a recrystallization in the most stable form, polymorph E. In the neighborhood of 230° C. polymorph E melts with an associated enthalpy of 105 J/g. This enthalpy is comparable with the enthalpy of pure polymorph E (i.e., about 114 J/g). This suggests that all polymorph A was transformed into polymorph E.

Stability of Polymorph E

To verify the stability of polymorph E, trials were performed at the laboratory scale, by putting polymorph E in competition with compound (I) (polymorph A) and with the THF solvated form in mixtures of solvent.

Polymorph E was first put in competition with compound (I) (polymorph A) (mixture 50/50, w/w) in ethanol/THF 80/20% v/v. This stability test was performed at ambient temperature under magnetic stirring for 24 hours, then the solid was filtered, dried, then analyzed by X-ray powder diffraction. Polymorph E was obtained. Similar experiments were performed in ethanol 100% at various concentrations. Polymorph E was always obtained.

Polymorph E stability also was tested as a suspension in 100% ethanol at room temperature, seeded with compound (I) (polymorph A). After 24 hours, X-ray powder diffraction analysis showed only polymorph E.

Polymorph E was also put in competition with the solvated form of compound (I) obtained in from THF. A mixture of the THF solvated form and polymorph E (50/50, w/w) was left under stirring for 24 hours in 40V of THF/ethanol (50/50, v/v) at room temperature. At the end, only polymorph E was present.

Polymorph E proved to be more stable than the polymorph A of compound (I) and more stable than the THF-solvated form under the conditions described above. In light of its superior performance characteristics, polymorph E was selected as the crystal form of N-(3-{[(2Z)-3-[(2-chloro-5- methoxyphenyl)amino]quinoxalin-2(1H)-ylidene]sulfamoyl}phenyl)-2-methylalaninamide for use in pharmaceutical compositions.

Tables

TABLE 1

List of most significant peaks of FIG. 1 (Polymorph E)

| Peaks (2 theta) | Intensity | Relative Intensity |
|---|---|---|
| 6.1 | 220 | 18 |
| 9.8 | 419 | 34 |
| 10.1 | 483 | 39 |
| 11.5 | 118 | 10 |
| 12.2 | 336 | 27 |
| 12.8 | 174 | 14 |
| 13.0 | 120 | 10 |
| 13.4 | 82.9 | 7 |
| 13.8 | 51 | 4 |
| 15.3 | 242 | 20 |
| 16.4 | 154 | 12 |
| 17.1 | 132 | 11 |
| 17.8 | 110 | 9 |
| 18.3 | 1237 | 100 |
| 18.6 | 213 | 17 |
| 18.8 | 620 | 50 |
| 19.1 | 220 | 18 |
| 19.5 | 168 | 14 |
| 19.8 | 198 | 16 |
| 20.7 | 81.8 | 7 |
| 21.2 | 62.4 | 5 |
| 21.4 | 72.1 | 6 |
| 22.1 | 157 | 13 |
| 22.5 | 68.7 | 6 |
| 23.2 | 570 | 46 |
| 23.7 | 733 | 59 |
| 24.4 | 939 | 76 |
| 24.9 | 58.8 | 5 |
| 25.6 | 150 | 12 |
| 26.0 | 51.5 | 4 |
| 26.6 | 64.4 | 5 |
| 27.8 | 228 | 18 |
| 28.3 | 387 | 31 |
| 28.6 | 77.6 | 6 |
| 28.9 | 122 | 10 |
| 29.4 | 158 | 13 |
| 30.0 | 93.6 | 8 |
| 30.6 | 343 | 28 |
| 31.6 | 149 | 12 |
| 32.3 | 99.1 | 8 |
| 32.9 | 72.9 | 6 |
| 33.2 | 80.4 | 6 |

TABLE 2

Figure 2:
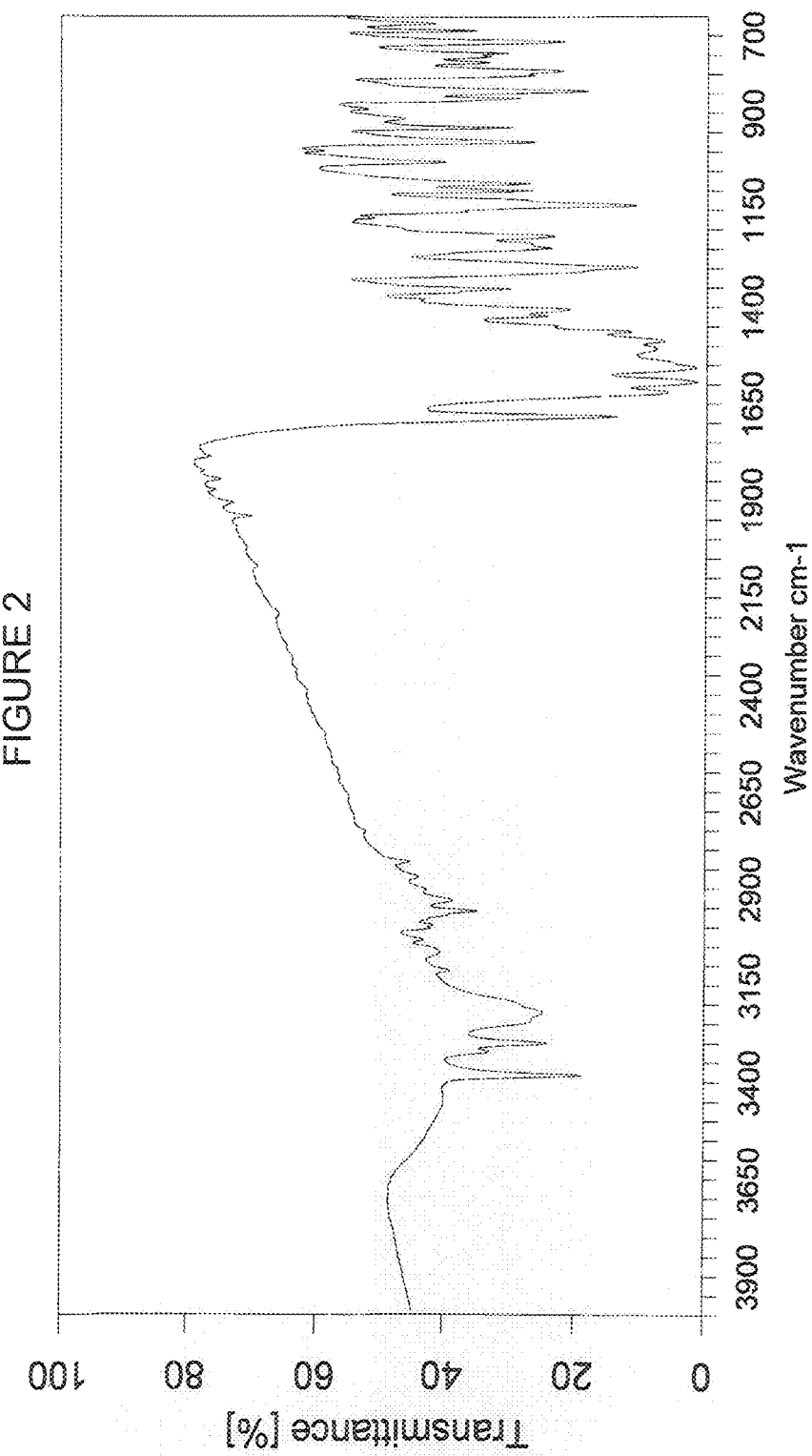
FIG. 2 depicts the FT-IR spectrum of polymorph E. The apparatus used was a Brucker Vertex 70 infrared spectrometer.

List of most significant peaks of FIG. 2 (Polymorph E) Wavenumber (cm$^{-1}$)

| |
|---|
| 3383.3 |
| 3300.3 |
| 3221.1 |
| 2957.8 |
| 2930.1 |
| 1682.0 |
| 1619.9 |
| 1593.1 |
| 1555.6 |
| 1486.9 |
| 1461.9 |
| 1404.6 |
| 1350.9 |
| 1296.2 |
| 1246.4 |
| 1216.0 |
| 1136.4 |
| 1097.7 |
| 1080.0 |
| 1023.5 |
| 973.3 |
| 935.4 |
| 912.3 |
| 860.5 |
| 842.1 |
| 790.5 |
| 767.3 |
| 744.3 |
| 714.5 |
| 685.3 |
| 666.3 |

TABLE 3

Most significant peaks of FIG. 13 (mixed DMAC/toluene solvate of compound (I))

| Peaks (2 theta) | Intensity | Relative Intensity |
|---|---|---|
| 5.5 | 201 | 6.4 |
| 8.0 | 156 | 5.0 |
| 9.7 | 256 | 8.2 |
| 10.3 | 115 | 3.7 |
| 11.0 | 125 | 4.0 |
| 13.6 | 204 | 6.5 |
| 14.9 | 204 | 6.5 |
| 16.0 | 152 | 4.8 |
| 16.5 | 268 | 8.6 |
| 17.0 | 104 | 3.3 |
| 17.6 | 177 | 5.7 |
| 18.3 | 1469 | 47.0 |
| 21.5 | 231 | 7.4 |
| 22.0 | 2031 | 65.0 |
| 23.6 | 349 | 11.2 |
| 26.1 | 307 | 9.8 |
| 27.6 | 3126 | 100.0 |
| 28.8 | 364 | 11.7 |
| 31.3 | 154 | 4.9 |
| 33.3 | 439 | 14.0 |
| 34.3 | 143 | 4.6 |

TABLE 4

Most significant peaks of FIG. 16 (DMSO solvate of compound (I))

| Peaks (2 theta) | Intensity | Relative Intensity |
|---|---|---|
| 6.8 | 100 | 26.5 |
| 7.1 | 102 | 27.1 |
| 7.6 | 307 | 81.5 |
| 11.8 | 58.1 | 15.4 |
| 12.8 | 45.3 | 12.0 |
| 13.6 | 56.4 | 14.9 |
| 16.5 | 75.8 | 20.1 |
| 17.4 | 127 | 33.7 |
| 18.2 | 82.5 | 21.9 |
| 18.6 | 238 | 63.0 |
| 19.8 | 377 | 100.0 |
| 20.5 | 197 | 52.2 |
| 21.2 | 144 | 38.1 |
| 22.3 | 144 | 38.1 |
| 22.9 | 98.0 | 26.0 |
| 24.0 | 111 | 29.4 |
| 24.3 | 76.4 | 20.2 |
| 25.0 | 156 | 41.4 |
| 25.5 | 74.1 | 19.6 |
| 26.3 | 84.5 | 22.4 |
| 26.9 | 95.8 | 25.4 |
| 29.9 | 111 | 29.4 |
| 31.0 | 89.9 | 23.8 |
| 36.7 | 110 | 29.1 |

TABLE 5

Figure 17:
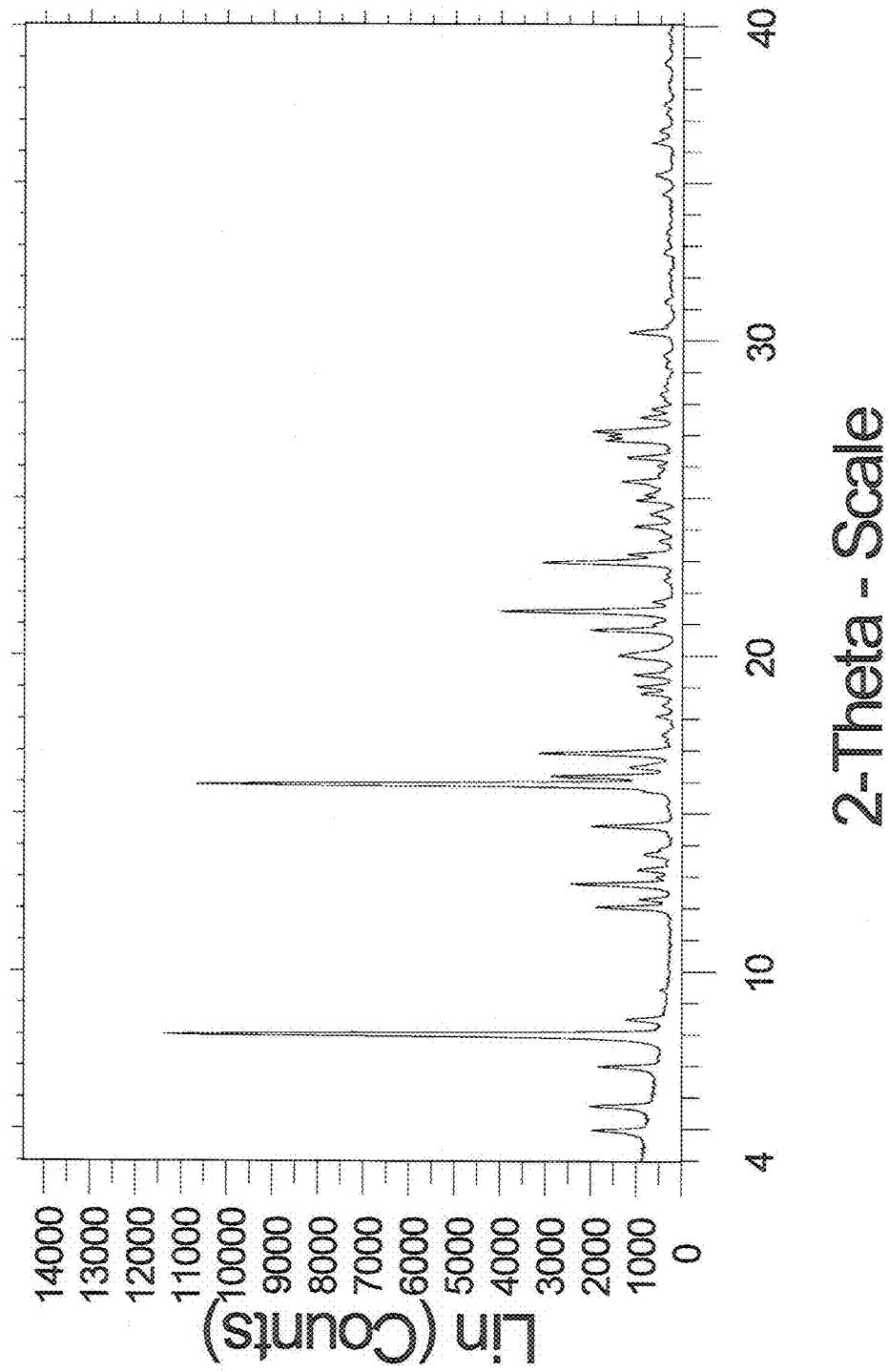
FIG. 17 depicts the X-ray powder diffraction pattern of polymorph A.

List of most significant peaks of FIG. 17 (Polymorph A)

| Peaks (2 theta) | Intensity | Relative Intensity |
|---|---|---|
| 5 | 953 | 8 |
| 9.8 | 1331 | 11 |
| 10.1 | 918 | 7 |
| 10.9 | 12667 | 100 |
| 11.2 | 7719 | 61 |
| 11.7 | 1415 | 11 |
| 12.8 | 801 | 6 |
| 13.1 | 377 | 3 |
| 14.2 | 900 | 7 |
| 14.7 | 2781 | 22 |
| 15.1 | 934 | 7 |
| 16 | 385 | 3 |
| 16.3 | 3321 | 26 |
| 16.6 | 2340 | 19 |
| 17.8 | 6746 | 53 |
| 18 | 8785 | 69 |
| 18.8 | 635 | 5 |
| 19.3 | 411 | 3 |
| 19.7 | 1337 | 11 |
| 20.2 | 1734 | 14 |
| 20.8 | 945 | 8 |
| 21.3 | 322 | 3 |
| 21.9 | 3268 | 26 |
| 22.5 | 10681 | 84 |
| 23 | 434 | 3 |
| 23.5 | 1351 | 11 |
| 23.7 | 1038 | 8 |
| 24 | 1340 | 11 |
| 24.4 | 292 | 2 |
| 24.7 | 1108 | 9 |
| 25 | 438 | 4 |
| 25.5 | 2813 | 22 |
| 25.7 | 3468 | 27 |
| 26.1 | 482 | 4 |
| 27 | 993 | 8 |
| 27.2 | 734 | 6 |
| 27.9 | 553 | 4 |
| 28.3 | 362 | 3 |
| 28.8 | 771 | 6 |
| 29.2 | 1243 | 10 |
| 29.6 | 1084 | 9 |
| 30 | 576 | 5 |
| 30.8 | 240 | 2 |
| 31.5 | 477 | 4 |
| 31.7 | 376 | 3 |
| 32.3 | 455 | 4 |
| 32.6 | 508 | 4 |
| 33.1 | 470 | 4 |
| 33.5 | 442 | 4 |
| 33.8 | 489 | 4 |
| 34.1 | 287 | 2 |
| 34.7 | 464 | 4 |
| 35 | 367 | 3 |
| 35.8 | 758 | 6 |
| 36.5 | 251 | 2 |
| 37.2 | 385 | 3 |
| 37.6 | 411 | 3 |
| 38.1 | 472 | 4 |
| 38.9 | 286 | 2 |
| 39.1 | 366 | 3 |
| 39.4 | 431 | 3 |

TABLE 6

Figure 18:
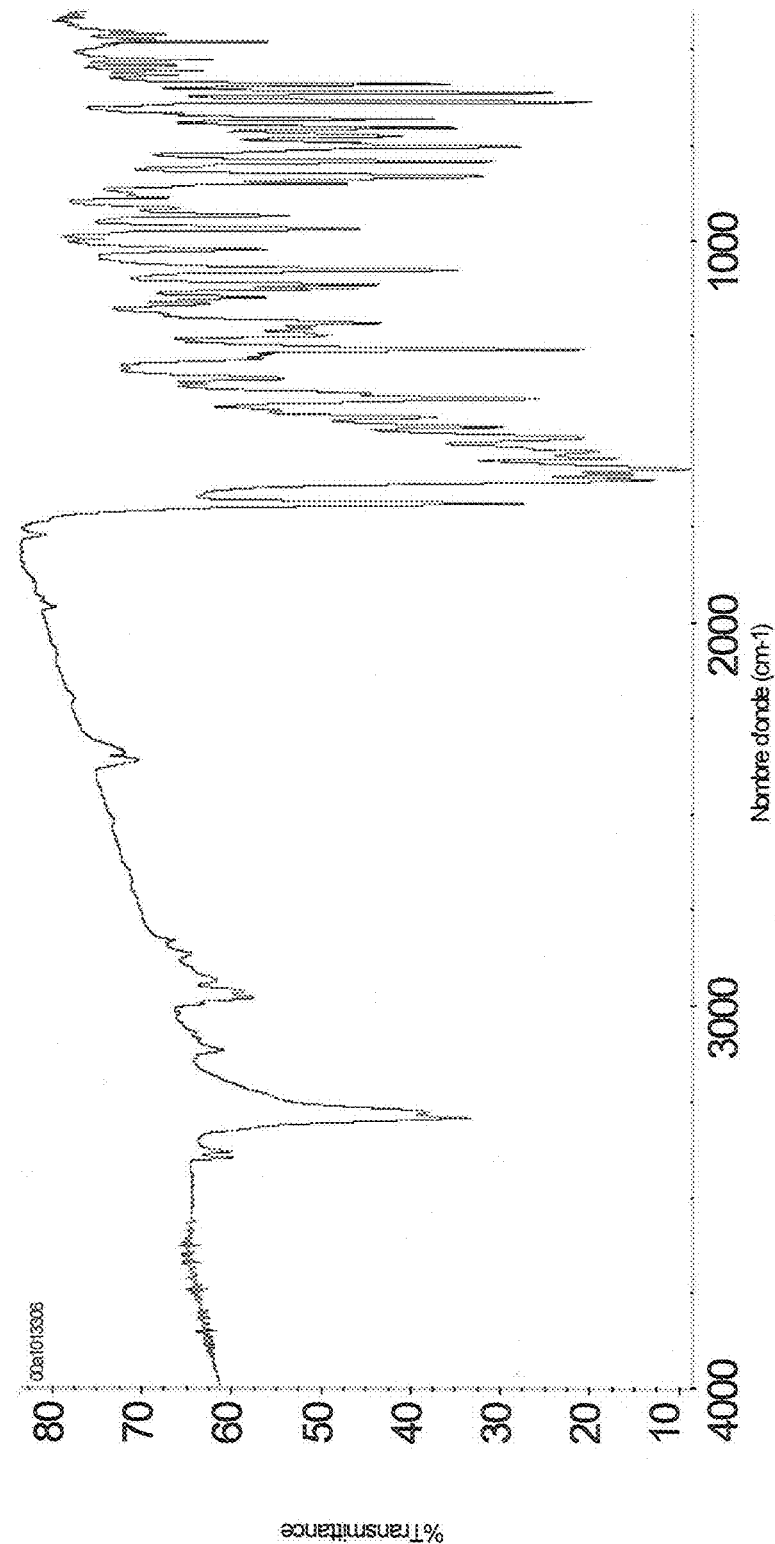
FIG. 18 depicts FT-IR spectra of polymorph A.

List of most significant peaks of FIG. 18 (Polymorph A) Wavenumber (cm$^{-1}$)

| |
|---|
| 3380.9 |
| 3293.1 |
| 2980.1 |
| 1689.2 |
| 1627.2 |
| 1611.9 |
| 1598.5 |
| 1571 |
| 1553.2 |
| 1516.5 |
| 1488.5 |
| 1463.8 |
| 1414.5 |
| 1362.2 |
| 1285.5 |
| 1248.3 |
| 1217.1 |
| 1148.3 |
| 1126.4 |
| 1114.9 |
| 1077.1 |
| 1023.3 |
| 969 |
| 934.6 |
| 851.6 |
| 832.8 |
| 793.7 |
| 755.8 |
| 727.3 |
| 705.5 |
| 683 |
| 637.8 |
| 613.8 |

TABLE 7

Figure 21:
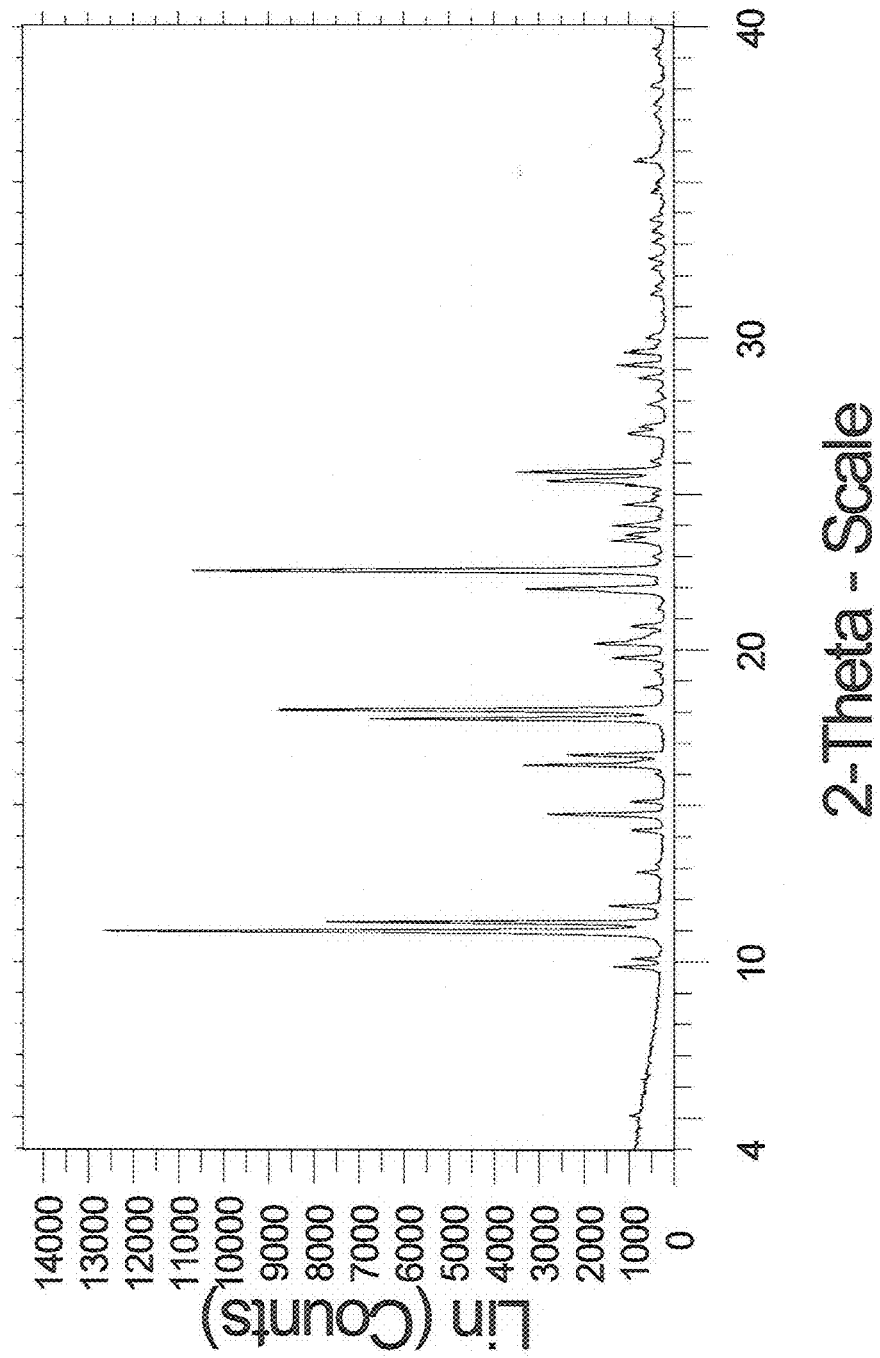
FIG. 21 depicts the X-ray powder diffraction pattern of pseudo-polymorph B.

List of most significant peaks of FIG. 21 (Pseudo-Polymorph B)

| Peaks (2 theta) | Intensity | Relative Intensity |
|---|---|---|
| 4.9 | 1951 | 17 |
| 5.7 | 1967 | 17 |
| 6.9 | 1810 | 16 |
| 8 | 11366 | 100 |
| 8.4 | 1188 | 11 |
| 9.4 | 443 | 4 |
| 10.2 | 267 | 2 |
| 11.5 | 257 | 2 |
| 12 | 1872 | 17 |
| 12.2 | 903 | 8 |
| 12.7 | 2413 | 21 |
| 13.2 | 932 | 8 |
| 13.7 | 824 | 7 |
| 14.6 | 1957 | 17 |
| 15.2 | 308 | 3 |
| 15.9 | 10677 | 94 |
| 16.2 | 2869 | 25 |
| 16.5 | 1112 | 10 |
| 16.9 | 3115 | 27 |
| 17.5 | 399 | 4 |
| 18.1 | 540 | 5 |
| 18.4 | 389 | 3 |
| 18.8 | 856 | 8 |
| 19 | 956 | 8 |
| 19.4 | 1029 | 9 |
| 20 | 1361 | 12 |
| 20.8 | 1983 | 17 |
| 21.4 | 3976 | 35 |
| 21.7 | 616 | 5 |
| 22.4 | 370 | 3 |
| 22.9 | 3046 | 27 |
| 23.2 | 1168 | 10 |
| 23.6 | 485 | 4 |
| 24.1 | 1014 | 9 |
| 24.5 | 675 | 6 |
| 25 | 998 | 9 |
| 25.2 | 738 | 7 |
| 25.5 | 1292 | 11 |
| 26 | 511 | 5 |
| 26.3 | 1180 | 10 |

TABLE 7-continued

List of most significant peaks of FIG. 21 (Pseudo-Polymorph B)

| Peaks (2 theta) | Intensity | Relative Intensity |
|---|---|---|
| 26.9 | 1587 | 14 |
| 27.1 | 1942 | 17 |
| 27.6 | 912 | 8 |
| 27.8 | 649 | 6 |
| 28.3 | 464 | 4 |
| 28.5 | 386 | 3 |
| 28.8 | 332 | 3 |
| 29.2 | 345 | 3 |
| 29.5 | 405 | 4 |
| 30.3 | 1151 | 10 |
| 31.3 | 370 | 3 |
| 32.2 | 272 | 2 |
| 32.8 | 401 | 4 |
| 33.2 | 309 | 3 |
| 33.5 | 340 | 3 |
| 34.7 | 431 | 4 |
| 35.3 | 566 | 5 |
| 35.8 | 258 | 2 |
| 36.3 | 647 | 6 |
| 36.7 | 484 | 4 |
| 37.3 | 346 | 3 |
| 37.5 | 400 | 4 |
| 38.1 | 295 | 3 |
| 38.2 | 287 | 3 |
| 38.9 | 370 | 3 |
| 39.3 | 277 | 2 |
| 39.8 | 315 | 3 |

TABLE 8

Figure 22:
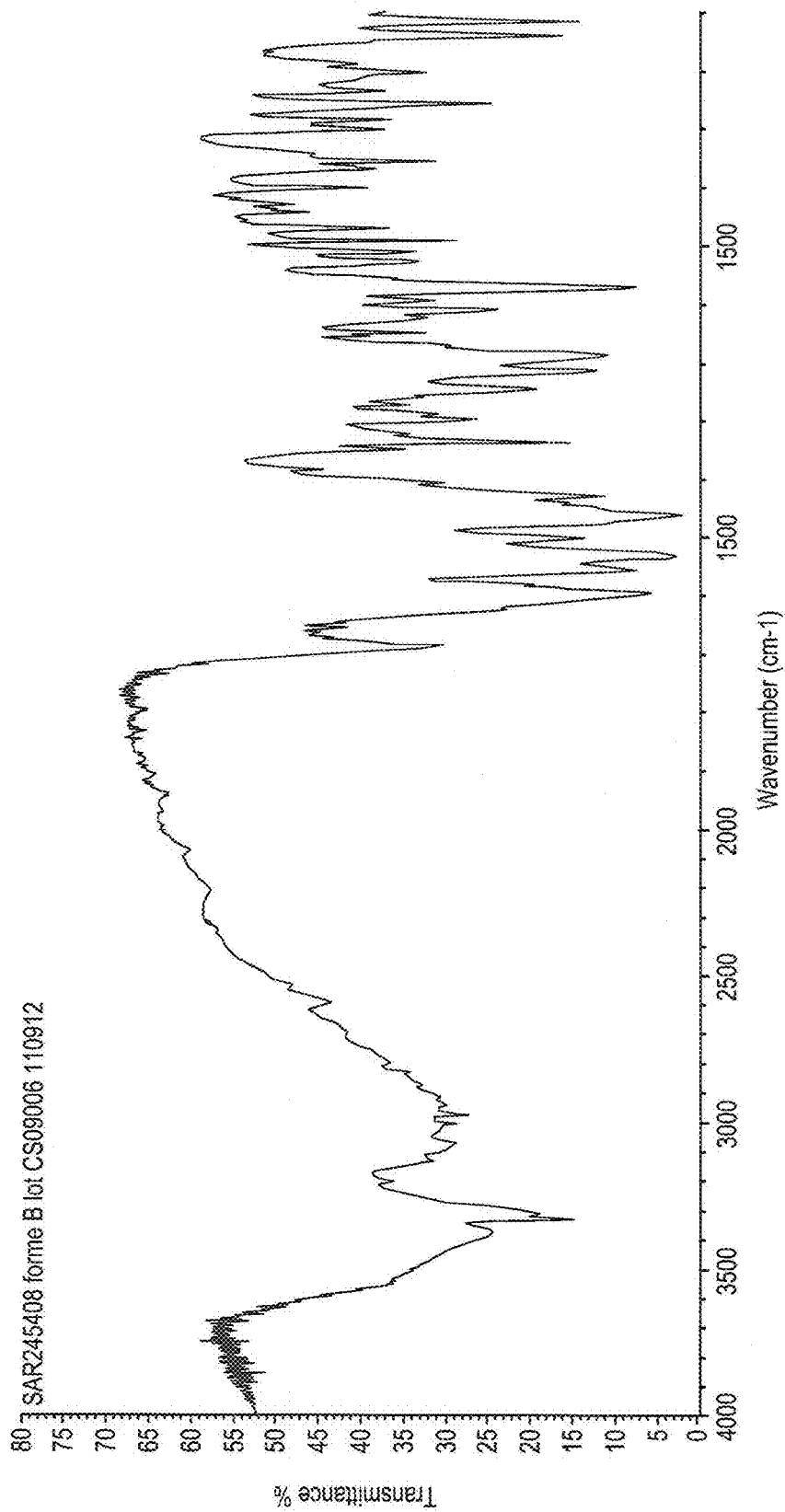
FIG. 22 depicts FT-IR spectra of pseudo-polymorph B.

List of most significant peaks of FIG. 22 (Pseudo-Polymorph B)
Wavenumber (cm$^{-1}$)

3368.2
3327.4
3067.6
2972.7
1685
1595.7
1555.6
1533.5
1500.6
1460.3
1429.6
1335.7
1297.3
1244.3
1213.8
1186.3
1109.2
1071.7
1026.9
1010.5
992.4
970.2
900.5
867.8
855.2
801.9
785.3
755.8
734.1
702.4
639.7
616.0

What is claimed is:

1. Polymorph E of N-(3-{[(2Z)-3-[(2-chloro-5-methoxyphenyl)amino]quinoxalin-2(1H)-ylidene]sulfamoyl}phenyl)-2-methylalaninamide.

2. The polymorph of claim 1, wherein the polymorph exhibits an X-ray powder diffraction pattern having characteristic peaks expressed in degrees 2 theta at angles of 18.3°±0.3° and 24.4°±0.3°.

3. The polymorph of claim 1, wherein the polymorph exhibits characteristic peaks at angles of 18.8°±0.3° and 23.7°±0.3°.

4. The polymorph of claim 1, wherein the polymorph exhibits characteristic peaks at angles of 10.1°±0.3° and 28.3°±0.3°.

5. The polymorph of claim 1, wherein the polymorph exhibits characteristic peaks at angles of 9.8°±0.3° and 23.2°±0.3°.

6. The polymorph of claim 1, wherein the polymorph exhibits characteristic peaks at angles of 9.8°±0.3°, 10.1°±0.3°, 18.3°±0.3°, 18.8°±0.3°, 23.2°±0.3°, 23.7°±0.3°, 28.3°±0.3° and 24.4°±0.3°.

7. The polymorph of claim 1, wherein the polymorph exhibits an X-ray powder diffraction pattern in accordance with FIG. 1.

8. The polymorph of claim 1, wherein the polymorph exhibits a Fourier transform infrared spectrum having characteristic peaks expressed in units of cm$^{-1}$ at values of 1682, about 1296 and about 1136.

9. The polymorph of claim 1, wherein the polymorph exhibits a Fourier transform infrared spectrum in accordance with FIG. 2.

10. The polymorph of claim 1, wherein the polymorph exhibits a differential scanning calorimetry thermogram having a characteristic peak at a temperature of 232.6±2° C.

11. The polymorph of claim 1, wherein the polymorph exhibits a differential scanning calorimetry thermogram in accordance with FIG. 3.

12. The polymorph of claim 1, wherein the polymorph exhibits a melting point of 230-235° C.

13. The polymorph of claim 12, wherein the polymorph has an enthalpy of fusion of 114 J/g.

14. The polymorph of claim 1, wherein the polymorph exhibits a thermogravimetry curve in accordance with FIG. 5.

15. The polymorph of claim 1, containing less than 1% by weight total impurities.

16. The polymorph of claim 1, containing less than 0.1% by weight total impurities.

17. A pharmaceutical composition comprising the polymorph of claim 1, and a pharmaceutically acceptable carrier or diluent.

18. The pharmaceutical composition of claim 17, wherein the composition comprises at least 50.0% by weight of polymorph E based on the total weight of N-(3-{[(2Z)-3-[(2-chloro-5-methoxyphenyl)amino]quinoxalin-2(1H)-ylidene]sulfamoyl}phenyl)-2-methylalaninamide in the composition.

19. The pharmaceutical composition of claim 17, wherein the composition comprises at least 99.0% by weight of polymorph E based on the total weight of N-(3-{[(2Z)-3-[(2-chloro-5-methoxyphenyl)amino]quinoxalin-2(1H)-ylidene]sulfamoyl}phenyl)-2-methylalaninamide in the composition.

20. The pharmaceutical composition of claim 17, wherein the composition is formulated for oral administration in the form of a pill, capsule, lozenge or tablet.

21. The pharmaceutical composition of claim 17, wherein the composition is in the form of a suspension.

22. A process for the preparation of the polymorph according to claim 1, which comprises the following steps: (a) dissolving N-(3-{[(2Z)-3-[(2-chloro-5-methoxyphenyl)amino]quinoxalin-2(1H)-ylidene]sulfamoyl}phenyl)-2-methylalaninamide in a first solvent, (b) optionally adding a second solvent, and (e) optionally seeding the mixture.

23. The process of claim 22, which comprises the following steps: (a) dissolving N-(3-{[(2Z)-3-[(2-chloro-5-methoxyphenyl)amino]quinoxalin-2(1H)-ylidene]sulfamoyl}phenyl)-2-methylalaninamide in tetrahydrofuran, (b) concentrating the mixture, (c) reducing the temperature of the mixture, (d) adding ethanol to the mixture, (e) seeding the mixture, and (f) lowering the temperature of the mixture.

24. The process of claim 22, which comprises the following steps: (a) dissolving N-(3-{[(2Z)-3-[(2-chloro-5-methoxyphenyl)amino]quinoxalin-2(1H)-ylidene]sulfamoyl}phenyl)-2-methylalaninamide in dimethylacetamide, (b) adding toluene, (c) lowering the temperature of the mixture, (d) filtering solids from the mixture and washing the solids, (e) suspending the filtered solids in ethanol, and (f) seeding the mixture.

25. The process of claim 22, which comprises the following steps: (a) dissolving N-(3-{[(2Z)-3-[(2-chloro-5-methoxyphenyl)amino]quinoxalin-2(1H)-ylidene]sulfamoyl}phenyl)-2-methylalaninamide in dimethylsulfoxide, (b) adding ethanol to the mixture, (c) filtering solids from the mixture, (d) suspending the solids in ethanol, and (e) seeding the mixture.

\* \* \* \* \*